(12) United States Patent
Hunter et al.

(10) Patent No.: US 10,379,119 B2
(45) Date of Patent: Aug. 13, 2019

(54) SYNTHETIC THREAD BASED LATERAL FLOW IMMUNOASSAY

(71) Applicant: Nplex Pty Ltd, Box Hill, Victoria (AU)

(72) Inventors: William Samuel Hunter, Bellbrae (AU); Sacha Marie Dopheide, Cremorne (AU); Samantha Irene Couper, Clyde North (AU); Mary Louise Garcia, Fitzroy North (AU); Joy Ji Liu, Southbank (AU); Christopher James Hurren, Winchelsea (AU)

(73) Assignee: Lumos Diagnostics IP PTY LTD, Box Hill, Victoria (AU)

( * ) Notice: Subject to any disclaimer, the term of this patent is extended or adjusted under 35 U.S.C. 154(b) by 333 days.

(21) Appl. No.: 15/309,077

(22) PCT Filed: May 7, 2015

(86) PCT No.: PCT/AU2015/050220
§ 371 (c)(1),
(2) Date: Nov. 4, 2016

(87) PCT Pub. No.: WO2015/168740
PCT Pub. Date: Nov. 12, 2015

(65) Prior Publication Data
US 2017/0074874 A1 Mar. 16, 2017

(30) Foreign Application Priority Data
May 7, 2014 (AU) .............................. 2014901679

(51) Int. Cl.
*G01N 33/558* (2006.01)
*G01N 33/543* (2006.01)

(52) U.S. Cl.
CPC ..... *G01N 33/558* (2013.01); *G01N 33/54386* (2013.01)

(58) Field of Classification Search
None
See application file for complete search history.

(56) References Cited

U.S. PATENT DOCUMENTS

| 3,996,345 A | 12/1976 | Ullman et al. |
| 4,058,732 A | 11/1977 | Wieder |
| (Continued) | | |

FOREIGN PATENT DOCUMENTS

| JP | 201232263 | 2/2012 |
| WO | 1998008093 | 2/1998 |

OTHER PUBLICATIONS

Hackh's Chemical Dictionary, McGraw-Hill, Inc. 1969.*
(Continued)

*Primary Examiner* — Christopher L Chin
(74) *Attorney, Agent, or Firm* — Carol L. Francis; Bozicevic, Field & Francis LLP

(57) ABSTRACT

The present disclosure generally relates to lateral flow immunoassay systems, devices and methods, for detecting analytes in biological samples. More specifically, the present disclosure relates to synthetic thread based lateral flow immunofluorescent assay systems, devices and methods. The lateral flow immunofluorescent assay devices can comprise one or more synthetic polymer threads defining at least a sample loading zone, a detection zone comprising an immobilized capture reagent that has affinity for a predetermined analyte in the sample, and an intermediate zone disposed between the sample loading zone and the detection zone, the intermediate zone comprising a fluorescent detection reagent for use in binding to a predetermined analyte in the sample to form a fluorescently labelled analyte, wherein the fluorescent detection reagent comprises fluorescently labelled microparticles that are associated, linked or coordinated to an analyte binding reagent that has affinity for a predetermined analyte in the sample, and wherein the one or more synthetic polymer threads are capable of carrying a fluid sample by capillary action from at least the sample loading zone to the detection zone.

21 Claims, 11 Drawing Sheets

(56) References Cited

U.S. PATENT DOCUMENTS

| | | | |
|---|---|---|---|
| 4,283,382 A | | 8/1981 | Frank et al. |
| 4,459,360 A | * | 7/1984 | Marinkovich ....... G01N 33/521 422/408 |
| 4,673,657 A | * | 6/1987 | Christian ............. B01J 19/0093 422/301 |
| 4,708,931 A | * | 11/1987 | Christian ............. B01J 19/0093 422/503 |
| 4,719,182 A | | 1/1988 | Burdick et al. |
| 5,122,452 A | | 6/1992 | Yamazaki et al. |
| 5,252,496 A | * | 10/1993 | Kang ............... G01N 33/54366 435/5 |
| 5,451,504 A | | 9/1995 | Fitzpatrick et al. |
| 5,622,871 A | * | 4/1997 | May ................. G01N 33/54386 422/504 |
| 2002/0150501 A1 | | 10/2002 | Robertson et al. |
| 2005/0227371 A1 | | 10/2005 | Gokhan |
| 2011/0189786 A1 | * | 8/2011 | Reches ................. B01L 3/5088 436/164 |
| 2015/0293087 A1 | | 10/2015 | Yoshida et al. |

OTHER PUBLICATIONS

Anfossi, Laura, et al., (2012) "A Lateral Flow Immunoassay for the Rapid Detection of Ochratoxin A in Wine and Grape Must", J Agric. Food Chem., 60(46):11491-7.

Anfossi, et al., (2013) "Optimization of a lateral flow immunoassay for the ultrasensitive detection of aflatoxin M1 in milk", Anal. Chim. Acta., 772:75-80.

Wong, et al, (2007) "Lateral Flow Immunoassay", Humana Press, pp. 170-181.

Van Dommelen, et al, (2010) "Alarmingly poor performance in Chlamydia trachomatis point-of-care testing", J. Sexually Transmitted Infections, 86:355-359.

Harma, et al., (2001) "Europium Nanoparticles and Time-resolved Fluorescence for Ultrasensitive Detection of Prostate-specific Antigen", Clinical Chemistry, 47(3):561-568.

Bangs Laboratories, (2013) "Covalent Coupling", Technical Note #205, 9 pages.

Ballerini, D. R., et al., (2011) "Flow control concepts for thread-based microfluidic devices", Biomicrofluidics, 5:014105-1-014105-13.

Kim, J., et al., (2013) "Sliced thread composite for low-cost multiplexed immunoassay", 17th International Conference of Miniaturized Systems for Chemistry and Life Sciences, Freiburg, Germany, pp. 937-939.

Li, X.; et al., (2009) "Thread as a versatile material for low-cost microfluidic diagnostics", ACS Applied Materials & Interfaces, 2:1-6.

Reches, M.; et al., (2010) "Thread as a matrix for biomedical assays", ACS Applied Materials & Interfaces, 2:1722-1728.

Safavieh, R., et al., (2009) "Yarn based microfluidics: from basic elements to complex circuits", Proceedings of MicroTAS 2009, Thirteenth International Conference on Miniaturized Systems for Chemistry and Life Sciences, Jeju, South Korea, pp. 685-687.

Zhou, G., et al., (2012) "Immunochromatographic assay on thread", Analytical Chemistry, 84:7736-7743.

* cited by examiner

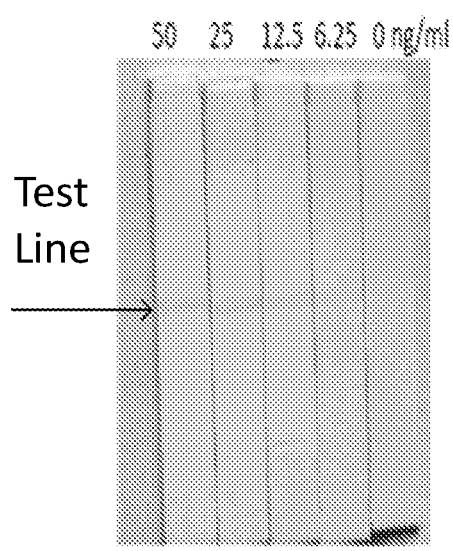
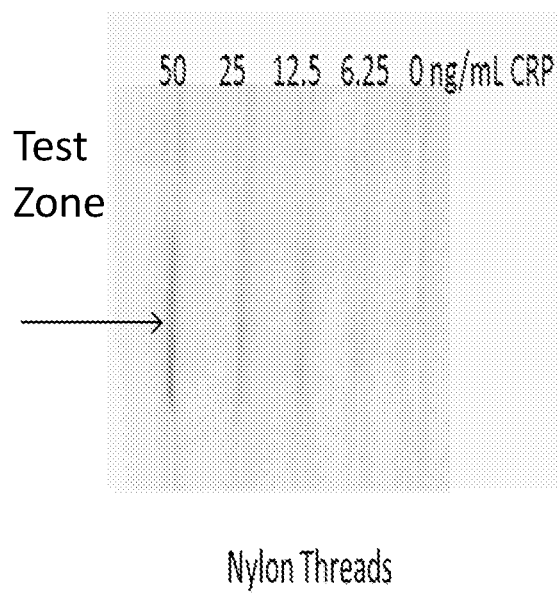
Nitrocellulose Membranes
Nylon Threads
Figure 6a
Figure 6b

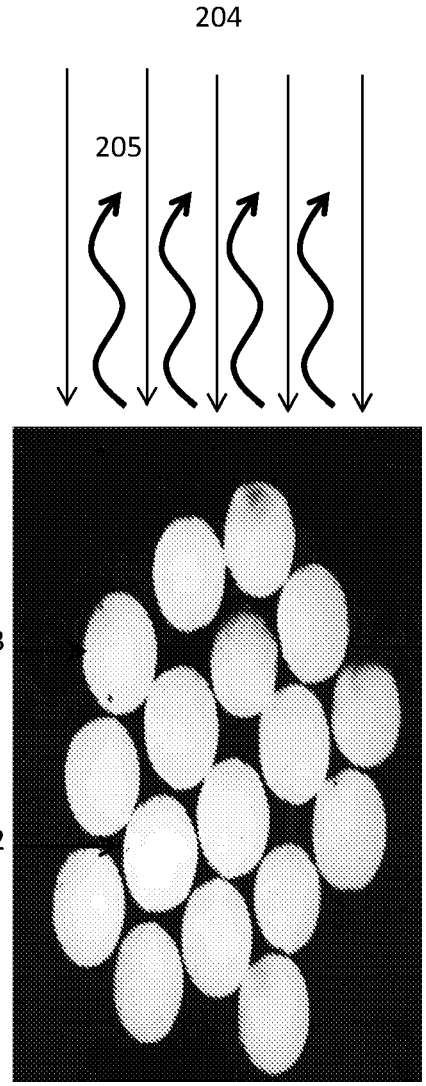
Figure 12
Figure 13

SYNTHETIC THREAD BASED LATERAL FLOW IMMUNOASSAY

FIELD

The present disclosure generally relates to lateral flow immunoassay systems, devices and methods, for detecting analytes in biological samples. More specifically, the present disclosure relates to synthetic thread based lateral flow immunofluorescent assay systems, devices and methods.

BACKGROUND

An important field of diagnostics is the use of rapid immunodiagnostic assays to provide speed, accuracy and simplicity in the diagnosis and testing in subjects, such as testing for diseases, conditions, microbes or drugs. A common form of such an assay is a lateral flow immunoassay, which is commonly employed in devices such as pregnancy test kits.

Lateral flow immunoassays are widely used for self-testing and in the clinical setting in view of their simplicity, speed and reliability, and involve a non-electrical method for rapidly detecting the presence of a specific analyte in a liquid sample, for example as described in United States Patent Application No. 2005/0227371.

Lateral flow immunoassays generally involve applying a liquid sample suspected of containing a predetermined analyte onto a porous carrier, and the liquid sample then traverses the porous carrier by capillary action. Different porous materials can be used for the porous carrier, and may differ in aspects such as pore size, wicking or flow rate, protein-binding aspects and pre-treatment. Essentially, all of the physical activities and chemical reactions take place in the porous carrier. The liquid sample is applied onto a sampling-end of the porous carrier (e.g. 'proximal end' or 'wet end') for a measured time or volume (e.g. 5 seconds or 2 drops). The liquid sample then migrates along the porous carrier by capillary action to the 'distal' or 'dry' end. The liquid sample can be pre-treated for optimized reaction with additional agents e.g. pH agents or buffers, surfactants, and/or blockers, which are typically impregnated into the porous carrier. The analytes in the sample can be 'labelled' for detection by using a labelled reagent (e.g. 'detection reagent') that has affinity for binding to a predetermined analyte. The sample can be labelled before contact with the porous carrier, or alternatively the porous carrier can include a 'labelling zone' where the sample mobilizes a labelled reagent that has been reversibly (temporarily) immobilized in the porous carrier. While the analyte is reacting with the mobilized labelled reagent, the liquid sample and mobilized labelled reagent migrates further within the porous carrier to a detection zone (e.g. 'capture zone') where a capture reagent (e.g. immobilised capture antibody) that binds the same analyte is immobilized to the porous carrier, usually in the form of a line. When analyte is present in the liquid sample, a 'sandwich' in the form of the labelled reagent:analyte:capture antibody is formed, and the resulting concentration of the labelled reagent leads to a detectable line appearing in the detection zone, which indicates a positive result. Any remaining sample liquid, together with the rest of the labelled reagent continues to migrate to a control zone and/or porous sink. Unbound labelled reagent that has not reacted with the predetermined analyte, and which remains in the porous carrier, contributes to a background signal that can reduce detection accuracy.

Nitrocellulose membranes are typically used in lateral flow immunoassays as a porous carrier material. However, some variability exists in nitrocellulose membrane materials arising from processes for preparing the materials, which can result in reduced accuracy and precision of tests. This variability in producing nitrocellulose membranes, which results in variation in wicking rates, causes a reproducibility problem where lateral flow tests have traditionally performed poorly for quantitative measurement, with assay coefficients of variability (CV) being commonly in the range 20-40%, such as described in *J Agric. Food Chem.* 2012 Nov. 21; 60(46):11491-7 and *Anal. Chim. Acta.* 2013 Apr. 15; 772:75-80. An assay CV of 25% means that the 95% confidence interval for a test result is the mean+/−50%. Such poor imprecision is not suitable for accurate measurements, particularly for quantitative measurement in determining the concentration of a target analyte in a sample, and on which clinical decisions may be based. An incorrect diagnosis may lead to incorrect clinical decision-making which may in turn lead to adverse health outcomes. Although other types of porous materials have been used as alternatives to nitrocellulose membrane materials, they also typically suffer from poor imprecision, particularly where analyte detection methods are reliant on low background noise.

A range of methods can be used for labelling an analyte and detecting the presence of a labelled analyte in a sample, for example colorimetric labels, radioisotopes and fluorescent labels, which have binding affinity for the predetermined analyte, may be used. For example, labelling using colorimetric latex beads has been described in U.S. Pat. No. 5,451,504. Conventional lateral flow tests using visual markers (such as colloidal gold labels) are known to perform poorly in terms of sensitivity. Other labelling techniques can also be problematic when used in rapid diagnostic assays for detecting small quantities of particular analytes in samples. Fluorescent labels have been used within some types of immunoassay systems, but their sensitivity has been typically limited by background fluorescence of the naturally-fluorescing porous carriers and constituents thereof, or from the presence of unbound fluorescent labels.

Consequently, there is a need to identify alternative and improved lateral flow immunoassay devices and systems that are accurate, cost-effective and rapidly enable the detection of a target analyte in a sample.

SUMMARY

The present disclosure is based on the inventors' research and development in lateral flow immunoassays, which can be used as a rapid and cost-effective diagnostic tool in accurately determining the presence of target analytes in samples.

The present disclosure provides synthetic thread based immunofluorescent assay systems, devices and methods, which at least in some embodiments may be used for qualitative identification and quantitative measurement of target analytes. The inventors, in the course of their research, identified problems associated with determining the accuracy and level of target analytes from samples using lateral flow immunofluorescent assays, and in particular assays that involve the use of fluorescent microparticles for binding to and detecting target analytes. The present disclosure is therefore also directed to providing lateral flow immunofluorescent assay devices comprising one or more synthetic polymer threads for use as a carrier of a fluidic sample by capillary action, and systems and methods comprising the devices that involve the use of fluorescently labelled microparticles for detecting target analytes.

In one aspect, there is provided a system for performing an immunofluorescent assay on a sample comprising:

a lateral flow immunoassay device comprising one or more synthetic polymer threads defining at least a sample loading zone, a detection zone comprising an immobilised capture reagent having affinity for a predetermined analyte in the sample, and optionally an intermediate zone disposed between the sample loading zone and the capture zone, wherein the one or more synthetic polymer threads are capable of carrying a fluid sample by capillary action from at least the sample loading zone to the detection zone;

a fluorescent detection reagent for binding to a predetermined analyte in the sample to form a fluorescently labelled analyte, wherein the fluorescent detection reagent comprises fluorescently labelled microparticles associated, coordinated or linked to an analyte binding reagent that has affinity for a predetermined analyte in the sample; and a fluorescent excitation source and detector for use in detecting a predetermined analyte that is bound to the fluorescent detection reagent and immobilised in the detection zone of the device by the capture reagent.

The system can be used for detecting the presence or level of a target analyte in a sample. In one embodiment, the system is used for quantitatively measuring the level (e.g. concentration) of a target analyte in a sample. The detection or measurement of a target analyte can be used to diagnose a condition or on which to base a clinical determination.

The immunofluorescent assay system may be a one-step immunofluorescent assay system. The immunofluorescent assay system may be a wet immunofluorescent assay system wherein the sample and a fluorescent detection reagent are mixed prior to contacting the sample to the sample loading zone of the device. The immunofluorescent assay system may be a dry immunofluorescent assay system wherein the immunofluorescent assay device comprises a fluorescent detection reagent. In an embodiment, the one or more synthetic polymer threads of the immunofluorescent assay device define an intermediate zone disposed between the sample loading zone and the detection zone. In a further embodiment, the fluorescent detection reagent is reversibly immobilised on the intermediate zone of the device for use in labelling a predetermined analyte for detection in the detection zone.

The sample may be pre-treated with one or more agents selected from the group consisting of pH or buffer agents, surfactants, filtering agents, and blocking agents. The sample loading zone of the device may comprise one or more agents selected from the group consisting of pH or buffer agents, surfactants, filtering agents, and blocking agents. The one or more agents may be immobilised on the sample loading zone. The detection zone may comprise one or more lines comprising the immobilised capture reagent. The capture reagent may be capture antibodies. The one or more synthetic polymer threads or device may further comprise one or more porous sinks or additional zones, for example control zones, reagent zones, spreading zones, blocking or filter zones, barrier zones or buffer zones.

In one embodiment, the analyte binding reagent is an antibody that has binding affinity for a predetermined target analyte. In another embodiment, the capture reagent is an immobilised capture antibody that has binding affinity for a predetermined target analyte.

The immunofluorescent assay system may provide single or multiplex assays. For example, the immunoassay device may comprise a plurality of threads for use in detecting two or more predetermined analytes in the sample.

In an embodiment, the one or more synthetic polymer threads are formed from synthetic polymers selected from the group consisting of polyamides, polyesters, polyethers, polyolefins, polycarbonates and polyurethanes. In another embodiment, the one or more synthetic polymer threads are formed from synthetic polyesters. The polyester may be selected from the group consisting of polyglycolic acid (PGA), polylactic acid (PLA), polycaprolactone (PCL), polyhydroxyalkanoate (PHA), polyhydroxybutyrate (PHB), polyethylene adipate (PEA), polybutylene succinate (PBS), poly(3-hydroxybutyrate-co-3-hydroxyvalerate (PHBV), polyethylene terephthalate (PET), polybutylene terephthalate (PBT, polytrimethylene terephthalate (PTT), and polyethylene naphthalate (PEN). In another embodiment, the one or more synthetic polymer threads are formed from synthetic polyamides. The polyamide may be nylon, for example a nylon selected from the group consisting of nylon-6,6; nylon-6; nylon-6,9; nylon-6,10; nylon-6,12; nylon-11; nylon-12 and nylon-4,6.

The fluorescently labelled microparticles may be fluorescently labelled polymer microparticles. The microparticles may be fluorescently labelled with fluorescent rare earth metal complexes. In one embodiment, the fluorescently labelled microparticles comprise polymer microparticles associated, linked or coordinated to fluorescent rare earth metal complexes. The rare earth metal complexes may comprise a lanthanide metal. The lanthanide metal may be selected from the group consisting of europium, terbium and samarium. In one embodiment, the rare earth metal is europium. The fluorescent rare earth metal complexes may be metal chelates of europium, terbium and samarium.

The polymer microparticles may have an average diameter (in nm) in the range of 100 to 5000, 150 to 2000, 200 to 1000, or 300 to 600. The average diameter (in nm) of the polymer microparticles may be at least about 100, 200, 300, 400, 500, 600, 700, 800, 900, or 1000. In one embodiment, the average diameter of the polymer microparticles is at least about 200 nm.

In another aspect, there is provided a lateral flow immunofluorescent assay device for use in performing an immunofluorescent assay on a sample, wherein the device comprises one or more synthetic polymer threads defining at least a sample loading zone, a detection zone comprising an immobilised capture reagent that has affinity for a predetermined analyte in the sample, and an intermediate zone disposed between the sample loading zone and the detection zone, the intermediate zone comprising a fluorescent detection reagent for use in binding to a predetermined analyte in the sample to form a fluorescently labelled analyte, wherein the fluorescent detection reagent comprises fluorescently labelled microparticles that are associated, linked or coordinated to an analyte binding reagent that has affinity for a predetermined analyte in the sample, and wherein the one or more synthetic polymer threads are capable of carrying a fluid sample by capillary action from at least the sample loading zone to the detection zone.

The immunoassay devices may comprise a substrate or housing for use in supporting the synthetic polymer threads.

It will be appreciated that embodiments described above for the immunofluorescent assay systems, where those embodiments relate to an immunoassay device, can also apply as embodiments for the above device.

In another aspect, there is provided a method for detecting an analyte in a sample comprising the steps:

a) obtaining a pre-treated sample comprising a fluorescently labelled analyte by contacting a sample to be tested for the presence of a predetermined analyte with a fluorescent detection reagent to thereby form the fluorescently labelled analyte, and wherein the fluorescent detection reagent comprises fluorescently labelled microparticles associated, linked or coordinated to an analyte binding reagent that has affinity for a predetermined analyte in the sample;

b) providing a lateral flow immunoassay device comprising one or more synthetic polymer threads defining at least a sample loading zone, a detection zone comprising an immobilised capture reagent having affinity for a predetermined analyte in the sample, and optionally an intermediate zone disposed between the sample loading zone and the detection zone;

c) contacting the sample loading zone of the lateral flow immunoassay device with the pre-treated sample obtained from step a) whereby the pre-treated sample is carried by capillary action from the sample loading zone to the detection zone, and the fluorescently labelled analyte binds with the capture reagent to be immobilised in the detection zone; and d) detecting fluorescently labelled analyte in the detection zone by fluorescent spectrometry.

In another aspect, there is provided a method for detecting an analyte in a sample comprising the steps:

a) providing a lateral flow immunofluorescent assay device comprising one or more synthetic polymer threads defining at least a sample loading zone, a detection zone comprising a capture reagent having affinity for a predetermined analyte in the sample, and an intermediate zone disposed between the sample loading zone and the detection zone, wherein the intermediate zone comprises a reversibly immobilised fluorescent detection reagent for use in binding to a predetermined analyte in the sample to form a fluorescently labelled analyte, wherein the fluorescent detection reagent comprises fluorescently labelled microparticles associated, linked or coordinated to an analyte binding reagent that has affinity for a predetermined analyte in the sample;

b) contacting the sample loading zone of the lateral flow immunofluorescent assay device with a sample to be tested for the presence of a predetermined analyte, whereby the sample is carried by capillary action from the sample loading zone to the intermediate zone and binds with the reversibly immobilised fluorescent detection reagent to form a fluorescently labelled analyte, the fluorescently labelled analyte then being carried by capillary action to the detection zone to bind with the capture reagent for immobilisation in the detection zone; and c) detecting fluorescently labelled analyte in the detection zone by fluorescent spectrometry.

The above methods can be used for detecting the presence or level of a target analyte in a sample. In one embodiment, the methods can be used for quantitatively measuring the level (e.g. concentration) of a target analyte in a sample. The detection or measurement of a target analyte can be used to diagnose a condition or on which to base a clinical determination.

It will be appreciated that embodiments described above for the immunofluorescent assay systems and devices, can also apply as embodiments for the above methods.

Other features, objects and advantages of the present disclosure and its embodiments will become apparent from the detailed description, examples and claims that follow.

BRIEF DESCRIPTION OF THE FIGURES

Embodiments of the present disclosure will now be further described and illustrated, by way of example only, with reference to the accompanying Figures in which:

FIG. 6a provides two photographs showing analyte detection of C-reactive protein in lateral flow immunoassays using a conventional nitrocellulose membrane (FIG. 6a) compared to a synthetic polymer thread (FIG. 6b) according to one embodiment of the invention;

FIG. 12 provides an electron microscope cross section of a natural fibre based cotton thread;

FIG. 13 provides an electron microscope cross section of a synthetic nylon thread.

DETAILED DESCRIPTION

Figure 1:
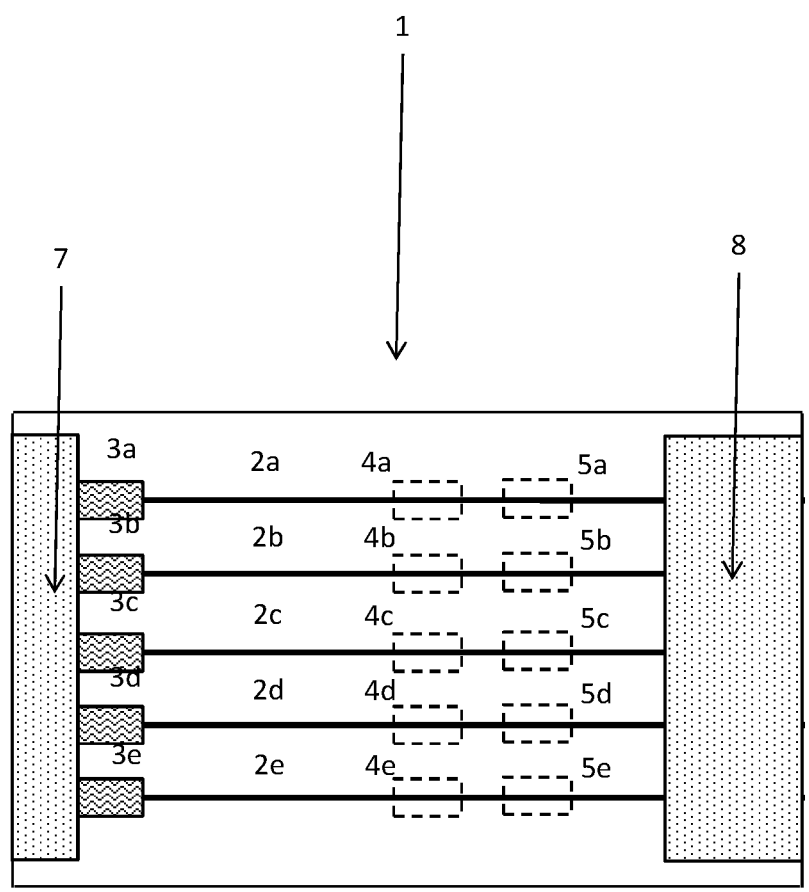
FIG. 1 provides a diagram showing an immunoassay device in plan view according to a first embodiment of the invention.

The present invention is described in the following various non-limiting embodiments, which relate to investigations undertaken to identify improved and alternative lateral flow immunoassay devices, systems and methods for rapidly and accurately determining the levels of target analytes in sample solutions. At least in some embodiments, it has been surprisingly found that lateral flow immunoassay devices comprising one or more synthetic polymer threads for use as carriers of fluidic samples by capillary action, can provide for improved qualitative and quantitative detection of target analytes, particularly for immunofluorescent assay devices, systems and methods using microparticle based fluorescent labels. Use of synthetic polymer threads in immunoassay devices can enable improved consistency and reproducibility of wicking rates and diagnostic capabilities of the devices, and at least in some embodiments, can reduce background fluorescence by reducing entrapment of unbound fluorescent microparticles that may be used in the porous carrier and therefore improving target analyte detection.

General Terms

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth.

Those skilled in the art will appreciate that the disclosure herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

Each example of the present disclosure described herein is to be applied mutatis mutandis to each and every other example unless specifically stated otherwise. The present disclosure is not to be limited in scope by the specific examples described herein, which are intended for the purpose of exemplification only. Functionally-equivalent products, compositions and methods are clearly within the scope of the disclosure as described herein.

The present disclosure is performed using, unless otherwise indicated, conventional techniques used in lateral flow immunofluorescent assays including fluorescent labelling, excitation and detection techniques. Such procedures are described, for example, in U.S. Pat. No. 4,719,182 or the literature reference "Lateral Flow Immunoassay, Wong et al, Humana Press, 2007, pages 170-181".

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be clearly understood that, although a number of prior art publications are referred to herein, this reference does not constitute an admission that any of these documents forms part of the common general knowledge in the art, in Australia or in any other country.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Specific Terms

Reference herein to a "sample" should be understood as a reference to any sample derived from a subject such as, but not limited to, a body fluid (e.g., blood or blood fraction such as serum or plasma, tears, urine, ascites, tears, sweat, saliva, excrement, gingival cervical fluid, tissue extract, synovial fluid or cerebrospinal fluid), cellular material (e.g. tissue aspirate), tissue biopsy specimens or surgical specimens. A "biological fluid sample", "fluid sample" or "body fluid" refers to any fluid that can be taken as a sample from the body of an organism and which may contain a detectable analyte or genetic material, for example blood or blood plasma from a human or animal subject. For lateral flow immunoassays, it will be appreciated that the sample applied to an immunoassay device is in the form of a liquid capable of capillary flow in the device, and the sample may be processed or additional agents or chemicals added to facilitate such liquidity and capillary flow.

An "analyte" includes but is not limited to proteins, macromolecules and small molecules that may be detected in a body fluid, such as an antigen or antibody present in a blood or blood plasma sample obtained from a human or animal subject.

The term "fluorescently labelled analyte", as used herein, means an analyte that has been labelled with a fluorescent species, such as a fluorescent detection reagent, that is capable of emitting fluorescence.

The term "antibody", as used herein, means a polyclonal or monoclonal whole immunoglobulin, e.g., IgG, IgM, IgA, IgE and the like, or an immunoglobulin fragment, e.g., F(ab)2, F(ab')2, Fab, Fab' and the like, or a mixture thereof, and includes synthetic antibody.

As used herein, the term "diagnosis", and variants thereof such as, but not limited to, "diagnose", "diagnosed" or "diagnosing" includes any primary diagnosis of a clinical state or diagnosis of recurrent disease.

As used herein, the term "microparticle" means particles having a diameter between about 0.1 μm and 100 μm, for example greater than about 100 nm.

The term "synthetic polymer thread", as used herein, refers to a thread formed from a plurality of individual synthetic polymer fibres.

The term "polymer" includes copolymers, and the term "monomer" includes co-monomers.

Diagnostic Immunoassay Systems, Devices and Methods

The lateral flow immunoassay systems described herein can provide cost-effective, portable and rapid diagnostic systems requiring relatively small sample volumes for testing, with improved detection of target analytes, particularly when used with fluorescent detection methods, such as in lateral flow immunofluorescent assays.

The immunofluorescent assay systems described herein comprise the use of a lateral flow immunoassay device comprising one or more synthetic polymer threads that provide a porous carrier system. The synthetic polymer threads can be coated or impregnated with various agents and configured for assaying fluid samples by utilising capillary action. The immunofluorescent assay systems comprise the use of fluorescent detection reagents, which comprise fluorescently labelled microparticles that are associated, linked or coordinated to an analyte binding reagent, for labelling a predetermined analyte in the sample and detecting the analyte by use of fluorescent spectroscopy. It will be appreciated that in immunoassays the analyte binding reagents and analytes will typically be provided by complementary antibodies and antigens. It will also be appreciated that a capture reagent for immobilising the target analyte in the detection zone of the device will typically be provided by complementary antibodies or antigens, depending on whether the target analyte is an antigen or antibody.

The synthetic polymer threads define at least a sample loading zone for use in loading a fluid sample onto the thread, and a detection zone for use in immobilising and detecting the presence of a target analyte in the sample. The detection zone comprises an immobilised capture reagent having affinity for a predetermined analyte in the sample. It will be appreciated that the synthetic polymer thread is suitable for carrying a fluid sample by capillary action from at least the sample loading zone to the detection zone. However, other zones in the thread and variations in configurations may be provided. Other zones may include one or more reagent zones, spreading zones, blocking or filter zones, barrier zones or buffer zones etc. The zones are in fluidic communication with each other by capillary action, meaning that fluids, reagents and reaction products can pass between zones, other than the capture reagent immobilised in the detection zone. The zones may be separated, superimposed or adjacent.

The predetermined analytes in the sample can be 'labelled' for detection by using a fluorescent detection reagent that has affinity for binding to a predetermined analyte. The sample can be fluorescently labelled before contact with the porous carrier, or alternatively the porous carrier can include a 'labelling' or 'detection zone' (e.g. an intermediate zone) where the sample mobilizes a fluorescent detection reagent that has been reversibly (temporarily) immobilized in the porous carrier. The fluorescent detection reagent can comprise fluorescently labelled microparticles associated, linked or coordinated to an analyte binding reagent. The analyte binding reagent is typically a complementary antibody when the target analyte is an antigen, for example. While the analyte is reacting with the mobilized fluorescent detection reagent, the liquid sample and mobilized detection reagent migrate further along the porous carrier to the detection zone (which may also be referred to as the 'capture zone' or 'immobilization zone') where a capture reagent (e.g. antibody) that binds the same analyte (e.g. antigen) is fixed or immobilized to the porous carrier, usually in the form of a line. When analyte is present in the liquid sample, a complex is formed by the capture reagent binding to the mobilized fluorescently labelled analyte, and the resulting concentration of the fluorescently labelled analyte provides a detectable line appearing in the detection zone, which indicates a positive result. Any remaining sample liquid, together with the rest of the fluorescently labelled reagent continues to migrate past the detection zone, for example to a control zone, which can be configured to provide a second line indicating that sample has progressed through the detection and control zones and that the assay has provided a valid test result. The rest of the sample and the remaining fluorescently labelled reagent may then be configured to migrate to a porous sink. It will be appreciated that any mobile fluorescently labelled reagent that has not reacted with the predetermined analyte, and which becomes entrapped across other areas of the porous carrier, contributes to a background signal that can reduce detection accuracy.

The synthetic polymer thread may be provided with an intermediate zone disposed between the sample loading zone and the detection zone. The intermediate zone may be used to further separate the sample loading zone and detection zone, and may or may not include any additional agents. In one embodiment, a fluorescent detection reagent may be reversibly immobilised on the intermediate zone of the device. The process comprises the sample being carried by capillary action from the sample zone to the intermediate zone, where the analyte in the sample can bind to and mobilise the reversibly immobilised fluorescent detection reagent to form a fluorescently labelled analyte. The fluorescently labelled analyte is then carried from the intermediate zone by capillary action to the detection zone. The fluorescently labelled analyte can then be immobilised ('captured') in the capture zone by its binding to an immobilised capture reagent (e.g. capture antibody) having affinity for the predetermined analyte (e.g. antigen).

The immunoassay devices may comprise a single thread or multiple threads. The immunoassay devices may be used in single or multiplex assays, such as in determining one or more predetermined analytes. Various configurations of the devices may be provided. For example, the immunoassay device may comprise a plurality of threads each connected at a central point, where the central point provides a sample loading zone and the distal ends of each thread comprise detection zones. At least in some embodiments, the lateral flow immunoassay devices and systems described herein may be referred to as "one-step" immunoassays. The one-step immunoassays may be a "wet" or "dry" type immunoassay.

A "wet" one-step immunoassay includes one or more synthetic polymer threads (as a porous carrier) defining at least a sample loading zone, which may be located at a proximal end of a thread, and a detection zone, which may be located at a distal of the thread. Other zones may be provided before, between or after each of the sample loading zone and detection zone. In this "wet" system, the sample and a fluorescent detection reagent are mixed prior to contacting the sample to the sample loading zone of the thread. The fluorescent detection reagent (e.g. a fluorescently labelled antibody), specifically binds with a predetermined analyte (e.g. antigen) in the sample solution to form a fluorescently labelled analyte prior to being contacted to the sample loading zone. After the sample solution is placed on the sample loading zone of the thread, the sample solution moves by capillary action across the detection zone wherein the fluorescently labelled analyte becomes fixed to an immobilised capture reagent (e.g. immobilsed antibodies) in the detection zone. Because the analyte is fluorescently labelled, the detection zone can be detected for fluorescence if any analyte is present in the solution.

A "dry" one-step immunoassay includes one or more synthetic polymer threads (as a porous carrier) defining at least a sample loading zone, a detection zone, and an intermediate (labelling) zone disposed between the sample loading zone and detection zone. The "dry" assay differs from a wet assay by including the fluorescent detection reagent directly on the thread reversibly (temporarily) immobilised in the intermediate zone. A sample solution containing the analyte of interest is first placed on the sample zone. Through capillary action, the sample solution traverses the thread. As the analyte in the sample passes the intermediate (labelling) zone, any analyte becomes labelled with the fluorescent detection reagent to form a fluorescently labelled analyte. The fluorescently labelled analyte is mobilised and along with the sample solution continues to traverse the length of the thread to the detection zone. As discussed for the "wet" assay, the sample solution moves by capillary action across the detection zone wherein the fluorescently labelled analyte becomes fixed to an immobilised capture reagent (e.g. immobilised antibodies) in the detection zone.

Because the analyte is fluorescently labelled, the detection zone can be detected for fluorescence if any analyte is present in the solution.

A first embodiment of the immunoassay device for a dry "one step" immunoassay is shown in FIG. 1. In this diagram, the immunoassay device (1) consists of an exemplary five independent and parallel thread lanes (2a-2e), to provide a five-plex immunoassay test. As stated previously, the immunoassay device may consist of one thread lane, or a multiplicity of thread lanes depending on how many analyte targets are required to be measured.

In the example shown in FIG. 1, firstly the sample is loaded onto a porous sample pad (7). The role of the sample pad is to accept the sample, possibly to treat it in such a way that it is compatible with the assay, and to release the analyte to the assay. Exemplary sample pads may be made from cellulose, glass fibre, rayon, or other filtration media.

Secondly the sample is released from sample pad (7), sample is able to flow into a number of independent and parallel conjugate pads (3a-3e), each of which are in fluidic communication with sample pad 7. Each of these conjugate pads will contain a dried down immobilised conjugate, such conjugate being a detector antibody for a particular target of interest bound to a fluorescently labelled microparticle. When the sample flows into the conjugate pad, the drieddown conjugate is rehydrated and released. Subsequently, the rehydrated released conjugate in each thread lane will form an immunocomplex with any target antigen which is specific to the conjugate in that thread lane. Conjugate pads may be made from glass fibres, polyesters, or rayons.

Thirdly the analyte (possibly containing an immunocomplex to the target antigen) is released from conjugate pads (3a-3e) into thread lanes (2a-2e), each of which are in fluidic communication with their respective conjugate pads. Each of the thread lanes will allow the analyte to gradually wick along the longitudinal axis of each thread until a detection zone (4a-4e) is reached. At the detection zone within each thread lane, a dried down capture antibody is present on the thread, and that capture antibody is specific to the target antigen. Thus, in a particular thread lane if the fluorescently labelled immunocomplex containing the target antigen is present, it will bind to the capture antibody immobilised on the thread at the detection zone, and this will be subsequently registered as a machine-readable fluorescent signal correlating to a positive test result. Alternatively, if no target antigen is present, there should be no binding of the fluorescently labelled microparticles in the detection zone, and this will be subsequently registered as a machine-readable zero (or near-zero) fluorescent signal correlating to a negative test result.

Fourthly the analyte flows past detection zones (4a-4e) into control zones (5a-5e). At control zones (5a-5e), a further capture antibody is immobilised on the thread. This further capture antibody is typically a species specific antibody, specific for the detector antibody in the conjugate. In this way, a positive fluorescent signal at control zones (5a-5e) is used as a quality control signal to ensure that the assay has run through correctly.

Fifthly, the analyte flows past control zones (5a-5e) into a wick, or waste pad (8). The wick is in fluidic communication with the thread lanes and is designed to pull fluid out of the threads (using the capillary action within the threads), and hold it for the duration of the assay. The wick material is typically a high-density cellulose material.

Figure 2:
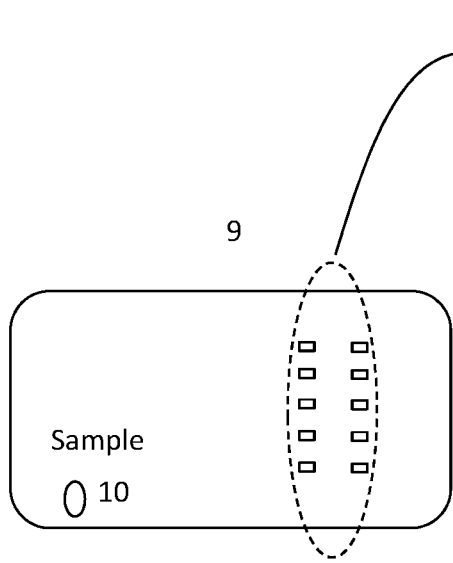
FIG. 2 provides a diagram showing a cassette for an immunoassay device in plan view.
Figure 4:
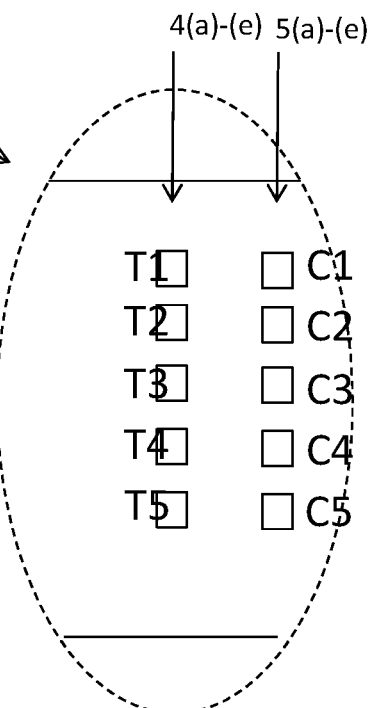
FIG. 4 provides a diagram showing an enlarged view of the test and control zone windows in a cassette for an immunoassay device in plan view.
Figure 3:
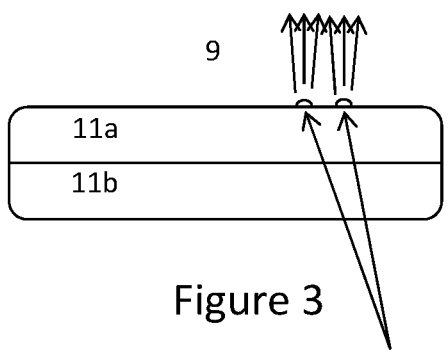
FIG. 3 provides a diagram showing a cassette for an immunoassay device in elevation view.

The immunoassay device shown in FIG. 1 may be housed in a plastic cassette (9) shown in FIG. 2. The plastic cassette may have an orifice (10) in its upper surface into which the sample is introduced, with this orifice exposing the sample pad (7) (as shown in FIG. 1). The plastic cassette may be comprised of upper and lower halves (11a and 11b) as shown in FIG. 3. The detection zones (4a-4e) and the control zones (5a-5e) on the threads are also exposed through windows in the upper half of the cassette as shown in FIG. 4. Each of these windows may be illuminated with fluorescent excitation light from an external instrument (not shown). As a result, any fluorescent microparticles present on or in the thread at locations (4a-4e, detection zones) or (5a-5e, control zones) will emit a fluorescent emission signal in proportion to the quantity of microparticles in these zones. These fluorescent emissions may be read by any known photo-detector in an external instrument (not shown). Fluorescent emissions may be guided or focussed into the photo-detector via a lens 12 shown in FIG. 3. In this way, the result of an exemplary five-plex assay may be reported as the independently read fluorescent emissions T1-T5 shown in FIG. 4. For quality control purposes, controls C1-C5 shown in FIG. 4 must also each be registered as a positive fluorescent signal to confirm that the test has run correctly.

Figure 5:
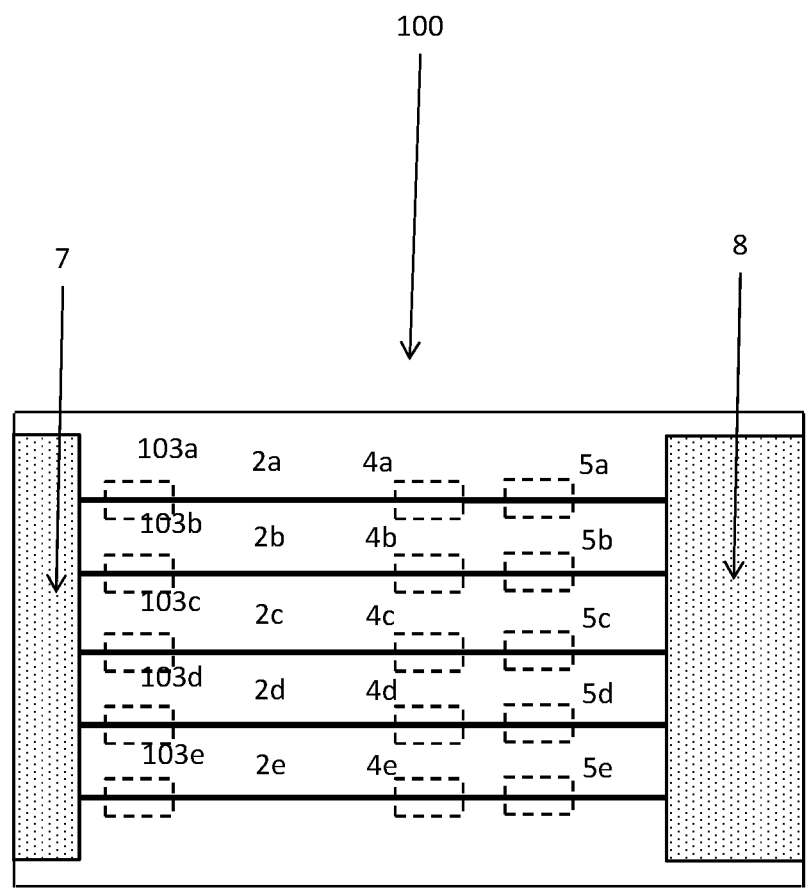
FIG. 5 provides a diagram showing an immunoassay device according to a second embodiment of the invention.

A second embodiment (100) of the immunoassay device for use in a dry "one step" immunoassay is shown in FIG. 5. This embodiment uses the same components as the first embodiment, with the exception that the conjugate pads 3a-3e are omitted. These conjugate pads are replaced with conjugate zones (103a-103b), which are zones within thread lanes (2a-2e) where the conjugate is dried down into the thread itself. In this embodiment, the wicking of the sample from the sample pad (7), through the thread lanes (2a-2e), and into the conjugate zones (103a-103e) rehydrates and releases the conjugate in zones (103a-103e) in the thread. In all other respects, the second embodiment (100) of the immunoassay device works in the same manner as the first embodiment (1), including the provision of the plastic cassette (9) shown in FIGS. 2-4.

In the second embodiment (100) of the immunoassay device, it is also possible for the conjugate zones (103a-103e) to be omitted in the case of "wet" one step immunoassay.

The liquid sample can be pre-treated for optimized reaction with additional agents e.g. pH agents or buffers, surfactants, and/or blocking reagents, additives, and other reagents to increase assay sensitivity. These are typically impregnated into the porous carrier, or into other components of the device (for example, the conjugate pad), however they may also be mixed with the liquid sample as separate reagents where the immunoassay device is part of a test kit.

The sample may be used alone as is commonly done with urine or serum compatible tests, or it may be mixed with a buffer specific to the test. This buffer may simply be a diluent/running buffer such as PBS, or similar, or it may be more complex and have specific components or extraction properties required to facilitate performance of the test, such as a cell lysis buffer.

The sample loading zone is where the fluidic capillary flow of the analyte-containing sample begins, and is a zone that preferably exhibits low analyte retention. Typically, a sample loading zone may be provided with a neutral proteinblocking reagent, followed by treatment to immobilize the blocking agent (e.g., lyophilization), which can increase wicking action. At least in some embodiments, the synthetic polymer threads as described herein can provide suitable wicking action without the use of blocking reagents. The sample zone may also be provided with additional immobilised agents to function as a mechanical filter by entrapping any undesirable particulates present in the sample solution.

Sample treatments within the sample zone typically include the filtering out of particulates or red blood cells, changing the pH of the sample, actively binding sample components that can interfere with the assay, and disrupting or lysing matrix components in the sample in order to release the analyte to the assay.

The detection zone may comprise a capture line of immobilised capture reagent (e.g. capture antibodies). Where capture antibodies are provided in the detection zone, they are typically chosen to bind with a second epitope on the target analyte (e.g. target antigen, since a first epitope of the antigen is bound to the fluorescent detection reagent). The target analyte thereby becomes concentrated at the capture line by binding to the thin line of antibodies on the synthetic polymer thread. As the fluorescently labelled analyte is carried over the detection zone, the second epitope on the analyte becomes bound to the antibodies at the capture line. As a result, the capture line becomes fluorescent if the target analyte is present in the sample. By placing the capture antibodies on the synthetic polymer thread in a thin line, the immunoassay system can detect very small quantities of analyte in the sample. Because each molecule of analyte can bind to a fluorescent detection reagent, the concentration of analyte in the sample correlates to the concentration of fluorescently labelled microparticles bound at the capture line. Consequently, a sample containing the target analyte will produce a fluorescent band across the capture line of the thread at a level that is directly proportional to the quantity of analyte in the sample.

Detection of fluorescence at the detection zone can be provided by a range of well-known methods. For example, an LED at a particular wavelength close to the excitation wavelength of the fluorescent microparticle can be used to deliver excitation light. An excitation filter may also be used. Emitted light from the capture line (possibly filtered by an emission filter) can then be detected by a fluorescence detector. Such a fluorescence detector may consist of one or more photodetectors, with each photodetector dedicated to analysing the fluorescent emission from a particular thread lane. The fluorescent detector may alternatively consist of a linear (one-dimensional) or area (two-dimensional) pixel array, with the fluorescent response from a particular thread lane dedicated to a particular pixel address on that array. The photodetector may be of a type which converts incident light to a square wave (such as the TAOS T235 device), where the frequency of the square wave is proportional to the incident light intensity, and the frequency is measured by a microprocessor. Light may be guided from the excitation LED to the detection zone via light guides, which may be, for example, unitary moulded components, or comprised of fibre optic bundles. Emitted fluorescent light may be guided from the detection zone to the photodetector via similar light guides. The excitation and emission light guides (in the case of fibre optics) may be bundled together to form a bifurcated probe at the detection zone. A scanning mechanism may be used to move each of the detection zone windows past a bifurcated probe to detect the assay result.

In a preferred embodiment, the light from the LED shall be at around 365 nm (UV) wavelength, and shall be suitable to excite a fluorescent response from microparticles dyed internally with Europium. These Europium microparticles emit a fluorescent response at 615 nm (orange), which may be captured by the photodetector. Either conventional fluorescent detection, or time-resolved fluorescent detection may be used with this approach. In the case where time-resolved fluorescent detection is used, emission and excitation filters are not required.

The immunoassay devices described herein may comprise a substrate or housing for use in supporting the synthetic polymer threads. The substrate or housing can be made of any inert material that does not interfere with the assay procedure, for example a flexible sheet, tape or moulded plastic. The housing can be used as a support to maintain the synthetic polymer threads in desired configurations and protect the synthetic polymer threads from contamination and damage during handling and storage. The housing can also be used to seal and separate synthetic polymer threads from each other, such as for multiplex assays, to prevent cross-contamination. The housing may be made of a transparent material.

Samples and Target Analytes

The immunoassay devices, systems and methods described herein can be used for assaying small volumes of biological samples, e.g., fluidic liquid samples. Biological samples that can be assayed using the diagnostic systems described herein include, e.g., urine, whole blood, blood plasma, blood serum, cerebrospinal fluid, ascites, tears, sweat, saliva, excrement, gingival cervical fluid, or tissue extract. In some embodiments, the volume of fluid sample to be assayed can be a drop of blood, e.g., from a finger prick, or a small sample of urine, e.g., from a newborn or a small animal.

Suitable analytes detectable by the immunoassay devices as described herein may be any for which a specific binding partner can be found. In general, most analytes of medical and biological significance can find specific binding partners in antibodies prepared against them or fragments of these antibodies. Suitable analytes include soluble analytes such as hormones, enzymes, lipoproteins, bacterial or viral antigens, immunoglobulins, lymphokines, cytokines, drugs, soluble cancer antigens, and the like. Also included as suitable analytes are hormones such as human chorionic gonadotropin (hCG), insulin, glucagon, relaxin, thyrotropin, somatotropin, gonadotropin, follicle-stimulating hormone, gastrin, bradykinin, vasopressin, and various releasing factors. A wide range of antigenic polysaccharides can also be determined such as those from *Chlamydia, Neisseria gonorrheae, Pasteurella pestis. Shigella dysentereae*, and certain fungi such as *Mycosporum* and *Aspergillus*. Another major group comprises oligonucleotide sequences which react specifically with other oligonucleotides or protein targets. A list of soluble analytes that may be determinable by the devices, systems and methods as herein described, is provided in U.S. Pat. No. 3,996,345, which is incorporated herein by reference.

A first exemplary assay for an analyte based on any of the aspects and embodiments described herein is for *chlamydia trachomatis* (CT). Rapid tests for CT at the moment based on the use of assays comprising nitrocellulose membranes together with colloidal gold visual markers typically suffer from poor sensitivity. For example, in a study of 772 women, it was found that a typical commercial rapid *chlamydia* test (Quidel Quickvue *Chlamydia* Test) had a sensitivity of 27% compared to the gold standard of nucleic acid testing [source: "*Alarmingly poor performance in Chlamydia trachomatis point-of-care testing*", van Dommelen et al, J. Sexually Transmitted Infections 2010; 86; pp 355-359]. Consequently, a rapid diagnostic device that could deliver 80-90% sensitivity for CT would be of high clinical utility. Furthermore, the invention could also be useful in contemporaneously diagnosing other sexually transmitted diseases with CT, for example a biplex assay of CT and NG (*Neisserea gonorrhoeae*), or a triplex assay of CT, NG, and *Trichomonas vaginalis*. The ability of the invention to accurately and rapidly diagnose several sexually transmitted diseases in parallel is also of high clinical utility.

A second exemplary assay for an analyte based on any of the aspects and embodiments described herein is for the protein biomarker Troponin I, which is used in the emergency room to diagnose acute myocardial infarction (AMI). To measure this biomarker accurately requires the ability to measure low analyte concentrations down to an analyte concentration of 100 pg/ml or better, with high repeatability (coefficient of variation <10%).

A third exemplary assay for an analyte based on any of the aspects and embodiments described herein is for the protein biomarker procalcitonin (PCT), which is a diagnostic marker for acute sepsis in the emergency room. PCT may be combined in a multiplexed diagnostic format with other markers such as C-Reactive Protein (CRP), and Interleukin 6 (IL-6) to enhance the diagnostic specificity.

It will be appreciated that the analyte binding reagent (of the fluorescent detection reagent) and the capture reagent each provide complementary binding partners to the predetermined target analyte. For example, where the target analyte is a proteinaceous species then the analyte binding reagent and capture reagent each provide a separate complementary binding partner for the proteinaceous species. Typically, the proteinaceous species is an antibody or an antigen. In the example where the target analyte is an antigen, then the analyte binding reagent and capture reagent can each provide a binding partner to a separate epitope of the target antigen, such as where the analyte binding reagent provides a first antibody for binding to a first epitope of the target antigen and the capture reagent provides a second antibody for binding to a second epitope of the same target antigen. It will be appreciated that the term "antibody", as used herein, means a polyclonal or monoclonal whole immunoglobulin, e.g., IgG, IgM, IgA, IgE and the like, or an immunoglobulin fragment, e.g., F(ab)2, F(ab')2, Fab, Fab' and the like, or a mixture thereof, and includes synthetic antibody. Antibodies and antibody fragments which specifically bind a wide variety of ligands are known, and would be readily understood by a person skilled in the field.

Synthetic Polymer Threads

It will be appreciated that an individual synthetic polymer thread is formed by the twisting together of a plurality of individual synthetic polymer fibres. In twisting together individual fibres, interstitial voids are formed between the individual fibres in the thread. The interstitial voids created in the process of forming a synthetic polymer thread provide a degree of porosity to the thread, in addition to any porosity that may be present within the material from which the individual fibres of the thread are formed. The porosity provided by the interstitial voids can traverse the length of the thread and provide one or more capillaries (i.e. channels). Capillary action (or wicking) in an individual thread occurs when liquid moves along a capillary formed from an interstitial void located between individual fibres, and results from intermolecular forces within and between the liquid and surrounding surface. If the diameter of the voids is sufficiently small, then the combination of surface tension (which is caused by cohesion within the liquid i.e. liquid-to-liquid attraction) and adhesive forces between the liquid and surface of the fibres/thread (i.e. liquid-to-surface attraction) act to draw (i.e. wick) the liquid along the thread by capillary action.

Synthetic polymer threads having substantially uniform sized capillaries can be prepared cost-effectively and reproducibly by known manufacturing processes, which typically involve the formation and spinning together of synthetic polymer fibres into threads. Synthetic polymer threads having substantially uniform sized capillaries can provide porous carrier materials for lateral flow immunofluorescent assays with an improved consistency in wicking rate, which can provide more accurate diagnostics such as quantitative determination of target analytes. Synthetic polymer threads having substantially uniform sized capillaries can also provide porous carrier materials for lateral flow immunofluorescent assays with lower background fluorescence, particularly when using fluorescent detection agents in the form of fluorescent microparticles, which can also result in more accurate diagnostics. Although not wishing to be bound by any theory, it is believed that threads having a substantially uniform size distribution can reduce the potential for entrapment of mobile unbound fluorescent detection agents, particularly entrapment of microparticles. Further advantages may also be provided by using individual synthetic fibres that are substantially non-porous, or at least have a substantially low pore size (i.e. diameter of largest pore) and pore size distribution (i.e. range of pore sizes). Again, without wishing to be bound by any theory, it is believed that substantially non-porous fibres further reduce the potential for entrapment of mobile unbound fluorescent detection agents within the individual fibres, particularly entrapment of microparticles. In other words, any microparticles that may be present would traverse the capillaries of the thread as opposed to any smaller pores or channels that may be present in an individual fibre (and in which the microparticles could become entrapped).

As mentioned above, the synthetic polymer threads formed from fibres have porosity arising from capillaries formed from interstitial voids between the fibres. The capillaries provide channels through which liquid molecules can pass. The average pore size provided by one or more capillaries may be in the range of about 5-30 microns. It will be appreciated that average pore size and pore density can be readily determined using scanning electron microscopy.

It will be appreciated that each synthetic polymer fibre of a synthetic polymer thread is formed from a synthetic polymer. It will also be appreciated that a synthetic polymer would not include natural polymer materials such as wood cellulose, cotton, silk and natural rubbers. For example, the synthetic polymer fibres are made from synthetic chemicals (monomers and copolymers), which are typically obtained from petrochemical sources, and may include fibres made from polyamides such as nylon, polyesters such as polyethylene terephthalate (PET), acrylic polyesters, aramids, phenol-formaldehyde (PF), polyvinyl chloride (PVC), polyolefins such as polypropylene (PP) and polyethylene (PE), and polyurethanes. The synthetic polymer fibres are typically formed from synthetic polymers (including monomers and copolymers) that may be particularly suitable for forming fibres and thread materials and may be suitable for use in immunoassays. For example, the synthetic polymers may have suitable hydrophilicity (arising from surface functional groups) and suitable mechanical properties (e.g. elasticity and tensile strength). The synthetic polymers can be selected and/or modified to control both the porous properties and the specific surface chemistries of the fibres and threads.

In an embodiment, the individual synthetic polymer fibres (of the threads) are formed from synthetic polymers selected from the group consisting of polyamides, polyesters, polyethers, polyolefins, polycarbonates and polyurethanes.

The synthetic polymers may be halogenated, such as fluorinated for example polyvinylidenefluoride or polyvinylchloride. In another embodiment, the individual synthetic polymer fibres of the threads are formed from synthetic polymers selected from the group consisting of polyamides and polyesters. General processes for producing polymer fibres and threads from a range of synthetic polymers are well known. The polymer fibres or the material can be further modified to increase hydrophilicity. The polymers may be blended or different types of polymer fibres combined.

In one embodiment, the individual synthetic polymer fibres of the threads are formed from polyesters. It will be appreciated that polyesters are polymers comprising repeating units linked by ester functional groups. The polyester may be thermoplastic or thermosetting. The polyester may be a homopolymer or copolymer. The polyester may be aliphatic, semi-aromatic or aromatic. The aliphatic polyester may be selected from the group consisting of polyglycolic acid (PGA), polylactic acid (PLA), polycaprolactone (PCL), polyhydroxyalkanoate (PHA), polyhydroxybutyrate (PHB), polyethylene adipate (PEA), polybutylene succinate (PBS), and poly(3-hydroxybutyrate-co-3-hydroxyvalerate) (PHBV). The semi-aromatic polyester may be selected from the group consisting of polyethylene terephthalate (PET), polybutylene terephthalate (PBT, polytrimethylene terephthalate (PTT), and polyethylene naphthalate (PEN). The aromatic polyester may be vectran, which can be formed from the polycondensation of 4-hydroxybenzoic acid and 6-hydroxynaphthalene-2-carboxylic acid.

In one embodiment, the individual synthetic polymer fibres of the threads are formed from polyamides. It will be understood that polyamides are polymers comprising repeating units linked by amide functional groups. The polyamide may be an aliphatic polyamide, polyphthalamide or aromatic polyamide (aramide). In one embodiment, the aliphatic polyamide is nylon. The nylon may be selected from the group consisting of nylon-6,6; nylon-6; nylon-6,9; nylon-6,10; nylon-6,12; nylon-11; nylon-12 and nylon-4,6.

The synthetic fibres may be coextruded fibres with two distinct polymers forming the fibre. The co-extruded fibres may be provided in the form of a core-sheath or side-by-side configuration.

In some embodiments, the thread is functionalized to enhance the absorptive and/or wicking properties using any of a number of known substances and methods. The fibre or thread may be coated or incorporated with agents to modify capillary action. Such agents may also be provided to enhance the ability of proteins (such as antibodies) to bind to the fibre or thread only at the test line location, or to block the ability of proteins to bind to the fibre or thread at locations only away from the test line. The agents may be incorporated into polymer material on forming the fibres or the fibre may be contacted with the agent for absorption thereon. The agent may be photo-activable, for example by UV light. One or more of the selected agents may be provided in one or more selected zones of the thread (for example at the test line location only).

Fluorescent Detection Reagents

Fluorescent spectroscopy is a well-known, sensitive and versatile optical analytical technique. In immunofluorescent assays, a sample containing an analyte tagged with a fluorescent species is irradiated with light of known spectral distribution within the excitation spectrum of the fluorescent species. The intensity of the resulting characteristic emission spectrum of the fluorescent species is determined and is related to the number of target analytes in the sample.

The lateral flow immunofluorescent assay devices, systems and methods, as described herein, involve the use of a 'fluorescent detection reagent' to label targeted analytes for detection by fluorescent emission in the detection zone of the thread. As previously described, the fluorescent detection reagents can be mixed with the sample prior to loading onto the thread (e.g. 'wet' one-step immunoassay) or may be temporarily immobilized at a location (e.g. intermediate zone) of the thread between the sample-loading zone and detection zone (e.g. 'dry' one-step immunoassay) for binding to a target analyte in a sample previously loaded onto the thread.

It will be appreciated that the fluorescent detection reagent comprises a fluorescent label that can selectively bind to a target analyte. To provide a fluorescent label with such selectivity for binding to a target analyte, the fluorescent label is associated, linked or coordinated to an analyte binding reagent that has affinity for a predetermined analyte in the sample. For immunoassays, the analyte binding reagent is usually an antibody that is selected to have affinity for a predetermined target analyte (e.g. antigen) in the sample. Alternatively, where the target analyte is an antibody, the analyte binding reagent can be an antigen selected to have affinity for the target antibody in the sample. Where the analyte binding reagent is an antibody, the linking of the antibody to a fluorescent label can be achieved by well-known techniques, for example the fluorescent label can be coordinated to an antigen having affinity for the antibody, and then the antibody associated for binding with the antigen of the fluorescent label, or a linking group can be used to covalently bond the antibody directly to the fluorescent label.

A large range of fluorescent detection reagents including fluorescent labels for use in immunoassays are well known, for example as described in U.S. Pat. Nos. 4,058,732, 4,283,382 and 4,719,182, which are incorporated by reference herein. The fluorescent labels can include fluorescently labelled particles, such as fluorescent microparticles.

It will be appreciated that the term "microparticle", as referred to herein, means particles having a diameter between 0.1 μm and 100 μm, for example greater than 100 nm, as opposed to the term "nanoparticle" that refers to particles having a diameter less than 100 nm.

An example of fluorescent particles for use as labels is described in U.S. Pat. No. 4,283,382, in which the label is a fluorescent microparticle comprising rare earth lanthanide complexes of europium bound to a latex microparticle. Fluorescent labels comprising europium (and other lanthanides) have been used in commercial immunoassays for some time. Time resolution techniques have been developed that isolate the specific signal of interest from the background signals. Unfortunately, these time resolution techniques take time to complete and involve determining whether the fluorescent signal was generated from a bound analyte or from background fluorescence. These techniques do not address problems resulting from any entrapment of unbound labelling reagent in the detection zone of the porous carrier. Consequently, the use of fluorescent particles in lateral flow immunoassays still suffer from high background noise associated with the entrapment of the unbound fluorescent labels in the porous materials. Such background noise is particularly problematic when using a lateral flow immunoassay to detect small quantities of a target analyte or quantitatively determine the level or concentration of a target analyte.

The amount of fluorescent emission available from a single fluorescent microparticle is correlated to the diameter of the microparticle, since a larger microparticle can be labelled by association with more fluorescent species, as described in a study by Harma et al entitled "Europium Nanoparticles and Time-resolved Fluorescence for Ultrasensitive Detection of Prostate-specific Antigen", Clinical Chemistry, March 2001, vol. 47, no. 3, p 561-568. For example, a 107 nm diameter microparticle can contain about $3.1 \times 10^4$ chelated Europium ions, while a 408 nm microparticle can contain about $2 \times 10^6$ chelated Europium ions. Consequently, larger diameter microparticles of about 400 nm can elicit a fluorescent response around 100× greater than the smaller diameter microparticles of about 100 nm. In view of this, the sensitivity of an immunofluorescent assay can be increased by using larger fluorescent microparticles. For example, U.S. Pat. No. 4,719,182, describes the use of fluorescent microparticles for obtaining improved sensitivity in immunoassays. However, it has been found by the present inventors that larger fluorescent microparticles can result in higher background noise in conventional porous carrier systems used in lateral flow immunoassays, which is presumed to arise from entrapment of the larger microparticles in the porous carrier materials. Consequently, the use of larger microparticles can become increasingly problematic and prohibitive in providing detection accuracy for target analytes. Surprisingly, the present inventors have identified that the use of synthetic polymer threads can reduce the background noise attributable by entrapment of microparticles in such immunoassay systems.

In an embodiment of the immunofluorescent assay devices, systems and methods as described herein, there is provided a fluorescent detection reagent comprising fluorescently labelled microparticles that are associated, linked or coordinated to an analyte binding reagent that has affinity for a predetermined analyte in the sample. In a further embodiment, the analyte binding reagent is an antibody that has affinity for a predetermined analyte in the sample.

Processes for coupling antibodies to such fluorescent microparticles are well known, and an exemplary protocol for performing such coupling can be found in Technical Note #205 from Bangs Laboratories, Inc. This procedure results in the formation of a detector antibody/detector microparticle conjugate, which can be loaded into a conjugate pad or conjugate zone in a thread as described previously.

Fluorescently Labelled Microparticles

The fluorescently labelled microparticles, as described herein, can be fluorescently labelled polymer microparticles (i.e. particles formed from polymers, copolymers or monomers, which are fluorescently labelled). The fluorescently labelled polymer microparticles can be formed by labelling polymer microparticles with fluorescent rare earth metal complexes. In other words, the fluorescently labelled polymer microparticles can comprise polymer microparticles associated, linked or coordinated to fluorescent rare earth metal complexes.

A large range of fluorescent rare earth metal complexes may be suitable as fluorescent labels for the polymer microparticles. Particularly suitable rare earth metal complexes, which provide sensitivity in detection and have a relatively long-lived fluorescence, are well known. The rare earth metal complexes comprise a rare earth metal such as a lanthanide metal. The lanthanide metal may be selected from the group consisting of europium, terbium and samarium. In one embodiment, the rare earth metal is europium. The fluorescent rare earth metal complexes may be provided in the form of a metal chelate, such as aromatic diketone chelates of europium, terbium and samarium, for example europiumbenzoylacetonate and europiumbenzoyltrifluoracetonate. Other examples of suitable chelating agents for the rare earth metals may include 1,3-diketones (e.g. acetylacetonate, benzoylacetonate, benzoylbenzoate, trifluoro-2-furylacetylacetone), phthalates, naphthoates (e.g. dinaphthoylmethide), dipyridines (e.g. 2,2'-bypyridine-1,1'-dioxide, 4,4'-dimethyl-2,2'-dipyridine), terpyridines (e.g. 2,2',6',2"-terpyridine) and phenanthrolines (e.g. phenanthroline isothiocyanate).

It will be appreciated that the polymer microparticles can be selected, prepared or processed to provide a low particle size distribution. The average diameter (in nm) of the polymer microparticles may be in the range of 100 to 5000, 125 to 2000, 150 to 1000, 175 to 500, or 200 to 400. The average diameter (in nm) of the polymer microparticles may be at least about 100, 200, 300, 400, 500, 600, 700, 800, 900, or 1000. The microparticles may be provided in ranges or values at or within these values. In further particular embodiments, the average diameter of the polymer microparticles is at least about 200 nm, in a range of about 200 to 400 nm, or about 300 nm.

Processes and polymers suitable for forming the loadable microparticles are well known. For example, suitable polymers may include those formed from one or more vinyl aromatic monomers, such as optionally substituted styrenes and vinyl naphthyls, or one or more optionally substituted ethylenically unsaturated monomers. Suitable monomers may comprise styrenes, acrylamides and acrylic acids. It will be appreciated that other polymers (and monomers and copolymers) may be suitable.

Processes for preparing (loading) the fluorescently labelled polymer microparticles are well known, and may generally involve incorporating the rare earth metal complexes into the polymer microparticles by gradually increasing the hydrophilicity of a solution of a hydrophobe in a water-miscible solvent in the presence of uncoagulated, undissolved loadable polymeric microparticles to a point at which substantially no hydrophobe remains dissolved in the watermiscible solvent. The amount of loading of metal complexes into the microparticles may be varied.

Fluorescent Detection

Suitable fluorescent detectors for use in detecting fluorescently labelled analyte at the detection zone in the devices are well known in the field.

The lateral flow immunofluorescent assay devices, systems and methods, as described herein, can have many applications involving low cost rapid diagnostics, for example sports medicine, infant/child diagnostics, diabetes monitoring, military, affordable diagnostics for less-industrialized countries, environmental or on-site testing. In addition, the methods are clinically useful in assisting patient management decisions. In that regard, quantitative measurements can improve clinical decisions concerning drug dose or treatment selections. For example, the methods can be used to determine the course of disease in a subject using the devices and systems as described herein. Disease course refers to changes in disease status over time, including diagnosis, disease progression (worsening) and disease regression or remission (improvement). Accordingly, the methods can involve the diagnostic measurement in a subject at two or more different time points, e.g., a first time and a second time, and comparing the change in amounts, if any, where the course of disease is determined based on these comparisons.

The invention is further illustrated by the following examples. The examples are provided for illustrative purposes only. They are not to be construed as limiting the scope or content of the invention in any way.

EXAMPLES

In accordance with embodiments of the present disclosure, lateral flow immunoassays comprising synthetic polymer threads as porous carrier materials, particularly for immunofluorescent assays with analyte detection reagents comprising fluorescent microparticles, were shown to provide accurate diagnostic systems that can be suitable for quantitative measurement of target analytes. The below examples provide comparisons between lateral flow immunoassay systems comprising porous carrier materials in the form of synthetic polymer threads, in accordance with some embodiments of the present disclosure, and porous carrier materials of a conventional nitrocellulose membrane and a natural fibre cotton thread.

Example 1: Comparative Study of Porous Carrier Materials in Visually Detectable Lateral Flow Immunoassays A lateral flow immunoassay comparative study was initially undertaken on two types of porous carrier materials, namely a natural cotton fiber based thread (DMC Cebelia) and a nitrocellulose membrane. The porous carrier materials comprised a sample loading zone at a proximal end and a detection zone comprising a capture antibody (separated from the sampling zone) at a distal end. The comparative study involved the use of samples comprising a predetermined analyte in the form of a dilution series of C-reactive protein (CRP), and a detection reagent comprising a detection label of colloidal gold markers coordinated to a CRP antibody. The antibody pairs used were matched pair of MAB 17071 Human CRP monoclonal antibodies (Clone 232007) from R&D Systems Inc.

The immunoassay study was conducted to determine the ability of the cotton thread and nitrocellulose membrane to detect different concentrations of CRP.

It was found that the limit of detection (LOD) for both a cotton thread and a nitrocellulose membrane was about 12.5 ng/ml. This result indicated that there was essentially no difference between the use of cotton threads and nitrocellulose membranes in their ability to detect the presence of target analytes. However, it was also found that the coefficient of variability (CV) of the wicking rate of the commercially available cotton threads was 26%, which was a poorer result than even that for commercial nitrocellulose membranes. This poor CV in terms of wicking rate leads to variations in the speed at which the detector antibody-antigen complex (label-antibody-CRP complex) traverses the testing zone. At the same analyte concentrations, a fast wicking rate leads to less intense test lines, and a slow wicking rate leads to more intense test lines. This variation in test line intensity (as occurs with nitrocellulose membranes) does not provide a robust enough platform for producing accurate quantitative assays.

In view of these results, it is considered that natural cotton fiber threads and nitrocellulose membranes, as porous carrier materials in rapid lateral flow immunoassays, do not provide accuracy for detecting levels of target analytes, and are particularly unsuitable as porous carrier materials for rapid lateral flow immunoassays where quantitative measurement of target analytes is required.

In trying to identify possible alternatives to natural fiber cotton threads and nitrocellulose membranes, synthetic polymer threads were prepared and tested. The detection capability of synthetic polymer threads was determined by using a conventional red-colored colloidal gold label and a dilution series of CRP, as described previously. The synthetic polymer threads were shown to have good performance in terms of detection capability. Two types of synthetic threads were made and tested, a polyester based thread and a nylon-6 based thread. Both the synthetic threads were prepared by extruding round synthetic fibers through a spinneret, and then machine twisting the fibers into a thread.

Nylon-6 synthetic threads were shown to have a detection limit of about 12.5 ng/ml of CRP using the colloidal gold visual marker as shown in FIG. 6b, which is the same as for the nitrocellulose membrane shown alongside in FIG. 6a. However, surprisingly the synthetic threads performed considerably better in terms of repeatability of wicking rate. In a number of replicates of a vertical wicking rate trial it was found that a nylon yarn performed with a CV of 5%, which is a 2.5-5× improvement on wicking rate CV available in cotton threads and nitrocellulose membranes. Consequently, the high wicking rate repeatability in machine extruded and machine spun synthetic threads, such as nylon, leads to an ability to perform repeatable quantitative assays.

Example 2: Comparative Study of Porous Carrier Materials in Lateral Flow Immunofluorescent Assays Comprising Fluorescently Labelled Microparticle A comparative study involving the use of fluorescently labelled microparticles in lateral flow immunofluorescent assays was undertaken between synthetic polymer threads and conventional nitrocellulose membranes and natural fiber cotton threads, as porous carrier materials. The immunofluorescent assay involved the use of fluorescent detection reagents comprising fluorescent microparticles. The fluorescently labelled microparticles used in this study were europium dyed microparticles, as described in U.S. Pat. No. 4,719,182, and a CRP immunoassay system was used in accordance with that of the previous example.

The study involved the use of a Millipore HFP 90 nitrocellulose membrane, a 300 nm europium dyed microparticle, and an Ocean Optics USB2000+ spectrometer in combination with an Ocean Optics 365 nm LED excitation source to analyze the fluorescent response of the Europium labelled CRP assay. Test strips were loaded into a fixture in a dark enclosure, and the fixture was driven by a servo motor at controlled speed. Excitation and emission filters were used to block any light entering the spectrometer which was not related to the emission from the Europium microparticles at 615 nm.

In the CRP assay, a CRP capture antibody was immobilized on the test strip (at a location 4 as shown in FIG. 1) using a BioDot programmable dispenser. A CRP detector antibody was conjugated to a 300 nm europium dyed microparticle in a separate step, and then mixed with CRP antigen in 2× dilution steps ranging from 150 ng/ml down to 0.15 ng/ml, with each of these dilutions being run (in 6 replicates) on separate test strips. After running each CRP dilution through the test strip, a wash step was performed using running buffer to ensure that any unbound europium labelled antibody complex (unbound fluorescent detection reagent) was cleared from the strip. Membrane blocking measures were also implemented to reduce the occurrence of europium labelled antibody (unbound fluorescent detection reagent) generally binding to all areas of the nitrocellulose membrane (and attributing to increased problematic background fluorescence). A negative sample (CRP=0 ng/ml) was performed as a control to provide an indication of any europium labelled antibody binding to the nitrocellulose membrane.

Figure 7:
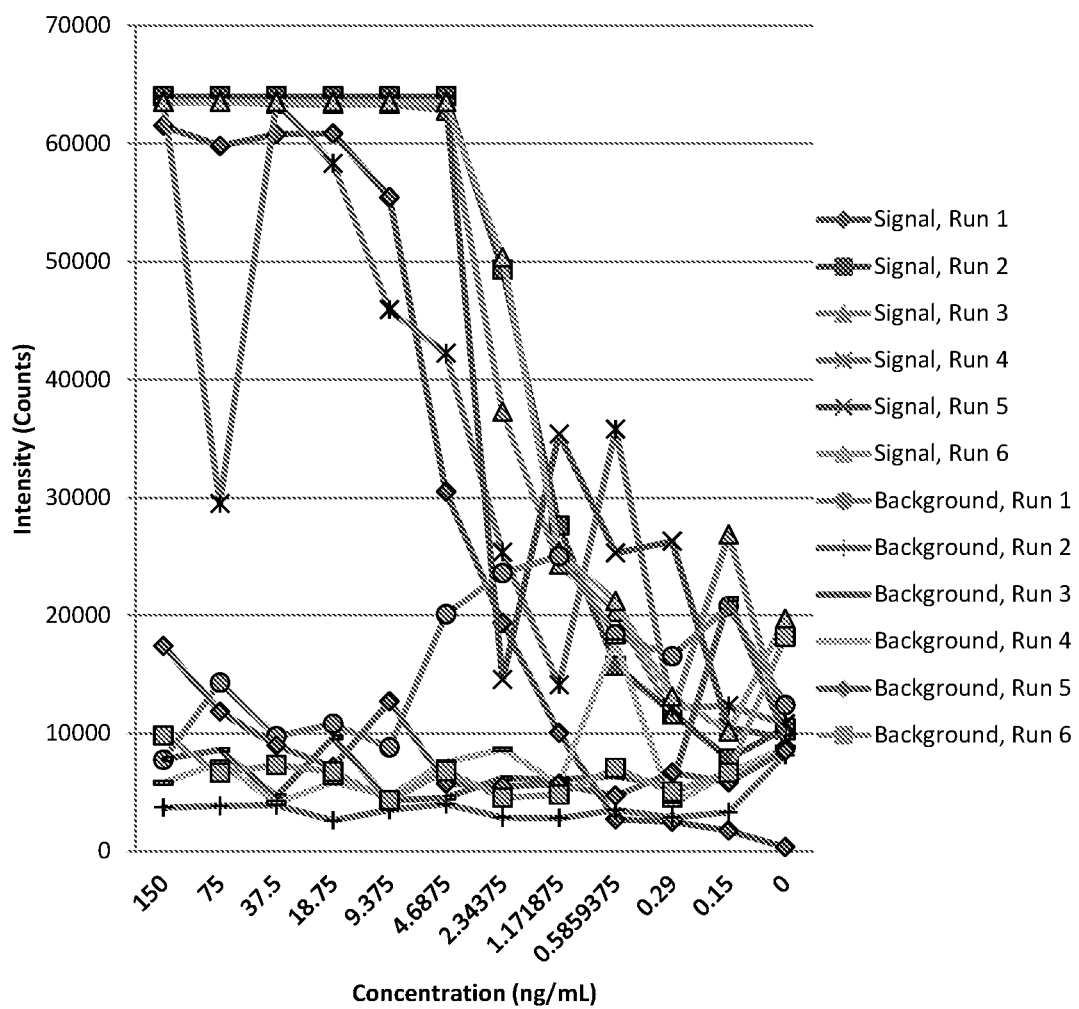
FIG. 7 provides repeat data on scans of fluorescent and background signals from nitrocellulose membranes used in a fluorescent microparticle labelled immunoassay when C-reactive protein was present in a titration series.

After analysing the replicate test strips at different CRP concentrations, it was surprisingly found that the fluorescent reading of the background in areas remote from the test line location were high and also varied widely. A dose response curve showing these results is included in FIG. 7. A recognized guideline for signal to background ratios in developing diagnostic tests is that the signal to background ratio should be higher than a ratio of 3. On this basis, it was found that only CRP concentrations above 9.375 ng/ml had a signal:background ratio consistently higher than 3.0. Consequently, it was considered this to be the LOD for a europium microparticle assay on a nitrocellulose membrane.

Figure 10:
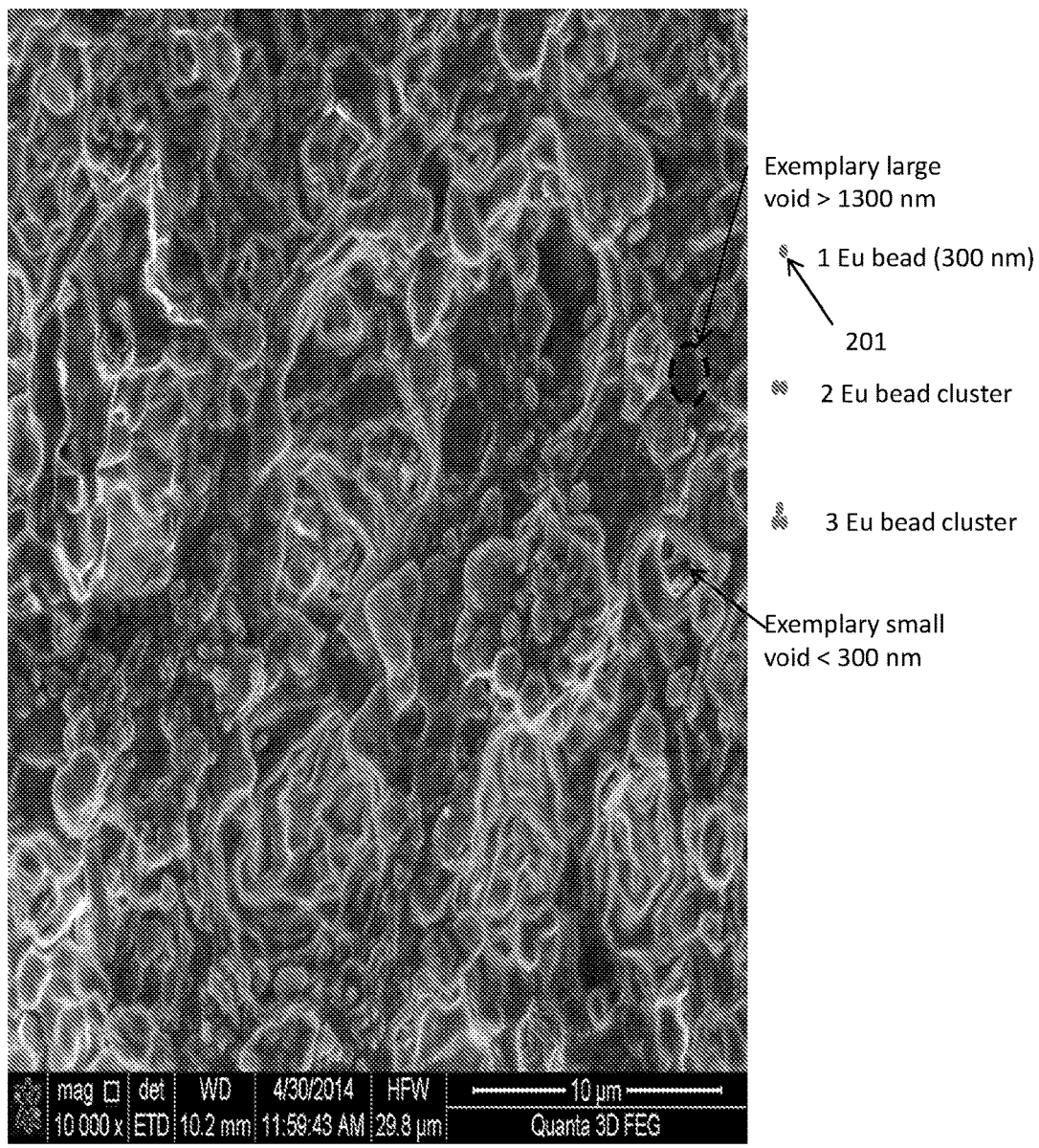
FIG. 10 provides an electron microscope 10,000× magnified image of a conventional nitrocellulose membrane used in lateral flow immunoassays.

This LOD on nitrocellulose using the europium fluorescent microparticles was approximately the same as compared to a conventional colloidal gold label, as described in Example 1 (LOD=12.5 ng/ml), it was a surprising finding that the LOD using the Europium microparticles was not as low as expected, and was only 1.3× better than the colloidal gold result. This appeared to be due to the presence of unwanted high background fluorescent signals present on the membrane in areas remote from the test line location. Although not wishing to be bound by any theory, it is presumed that the high background signal occurs as a result of the 300 nm europium microparticles becoming stuck in the highly variable pore structure of the nitrocellulose membrane. Shown in FIG. 10 is an electron microscope image of a nitrocellulose membrane at 10,000× magnification. This membrane is a high flow membrane (Millipore HF90) which is known to have a relatively large pore size for membranes used in lateral flow tests. In FIG. 10, we have found that, surprisingly, some of the pores in the membrane are smaller than the diameter of a Europium microparticle (<300 nm) (201), which would potentially cause such microparticles to become undesirably lodged in the membrane at a location other than the detection zone or control zone. Furthermore, we have also surprisingly found that the Europium microparticles may cluster together during wicking (refer to FIG. 14, and the accompanying description below), for example in clusters of 2 or 3 Europium microparticles, and such clusters are more likely to become undesirably lodged in the membrane at locations other than the test or control line. The undesirable lodgment of Europium microparticles at these locations in the membrane is unlikely to be able to be resolved by multiple wash steps, or by traditional membrane blocking measures (such as the application of casein or similar) to prevent non-specific binding, or by image analysis software compensation since the undesirable lodgment of these particles is due to the physical limitations of the membrane structure itself. The undesirable lodgment of these particles is likely to cause high unwanted background fluorescent signals at locations other than the detection or control zones, and these high background signals will substantially decrease the potential sensitivity of the assay.

Figure 11:
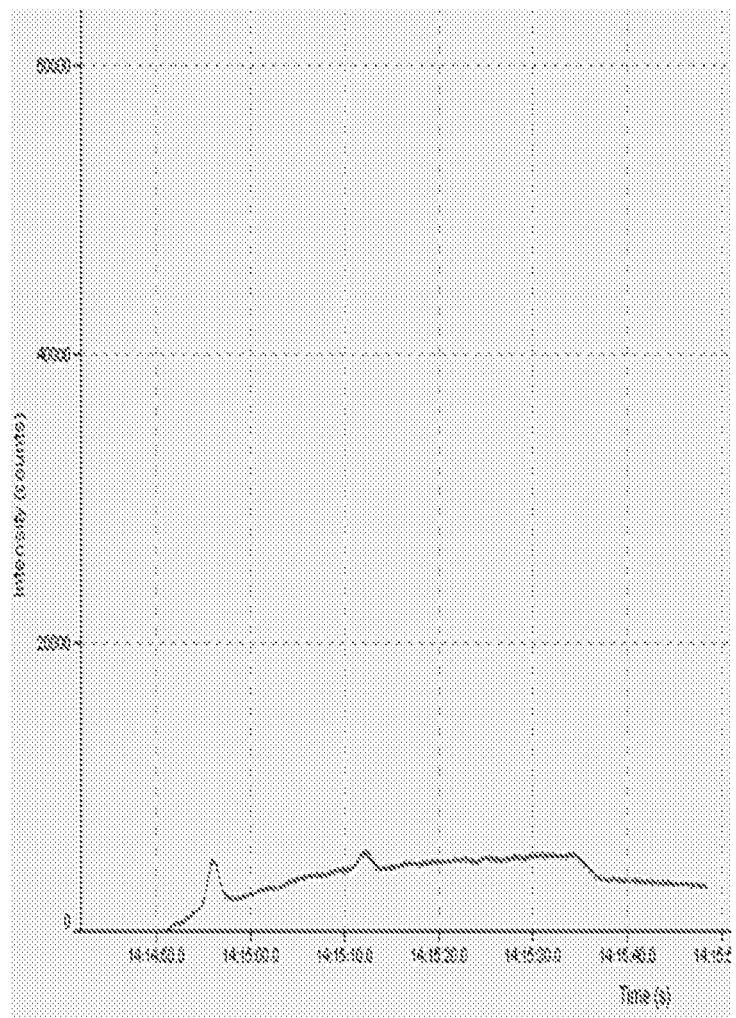
FIG. 11 shows a longitudinal fluorescent scan of a conventional nitrocellulose membrane when a negative C-reactive protein sample is used, and where the detection label is a 300 nm Europium microparticle.

In FIG. 11, we show a scan along the longitudinal direction of a nitrocellulose membrane, where a negative sample (0 ng/ml) of C-reactive protein was used. In this scan it can be seen that there is substantial fluorescent signals at all locations along the length of the test strip, and that the measured background fluorescence is as high as 6000 counts from this scan. This scan illustrates the undesirable lodgment problem described above, and the result is that positive CRP assays with signal levels below 6000 counts would be undesirably recorded as false negatives.

The only solution to the unwanted lodgment problem may be to use europium nanoparticles (for example 50 nm diameter, similar to colloidal gold). However, smaller such nanoparticles have several orders of magnitude lower fluorescent response than larger microparticles, and hence such a solution would negate the sensitivity benefit of using larger europium microparticles.

Figure 8:
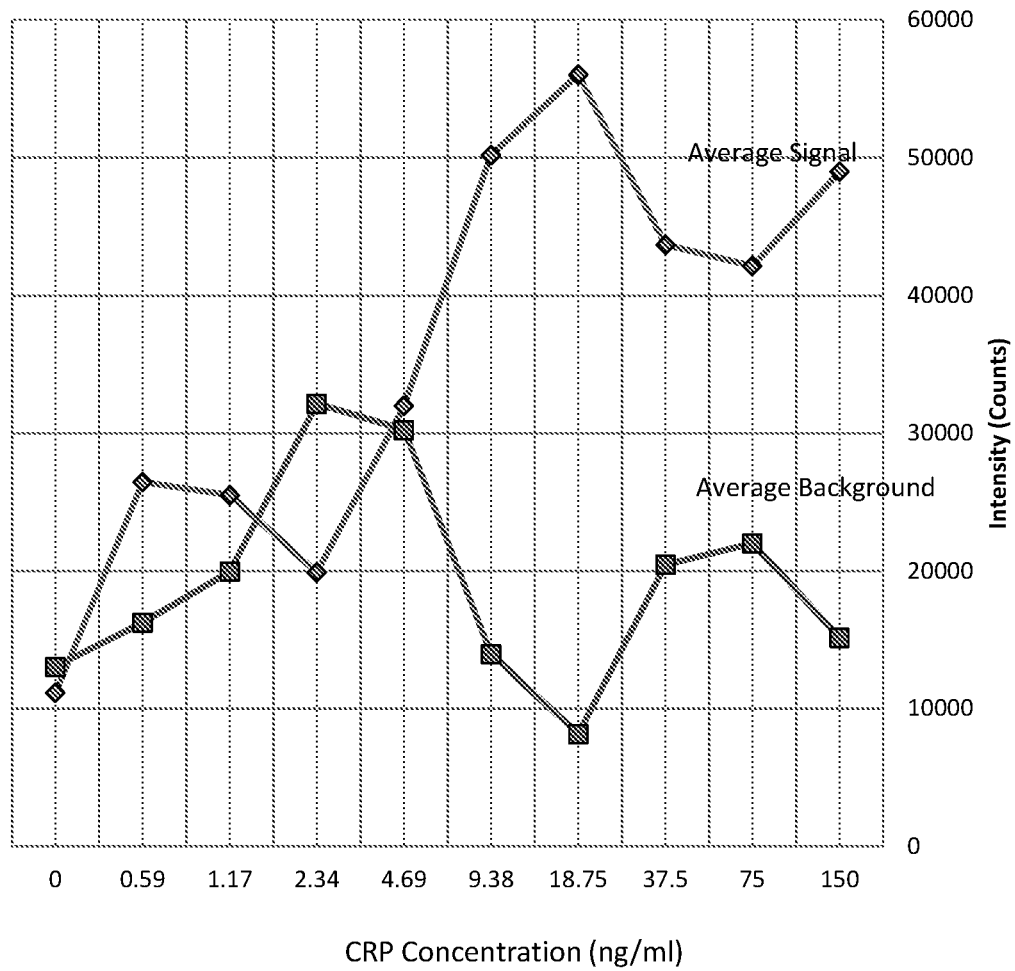
FIG. 8 provides a scan of fluorescent and background signals from a cotton thread used in a fluorescent microparticle labelled immunoassay when C-reactive protein was present in a titration series.

The same fluorescent CRP assay titration series was performed on a commercial cotton thread (DMC Cebelia), and it was found that the signal:background ratio and LOD for cotton threads was similar to conventional nitrocellulose membranes, as shown in the dose response curve in FIG. 8. Again, without wishing to be bound by any theory, it is presumed that this occurs because the cross-sectional structure of cotton threads (shown in FIG. 12) is also highly variable, and may undesirably entrap larger diameter microparticles at locations other than the test or control zones.

Figure 9:
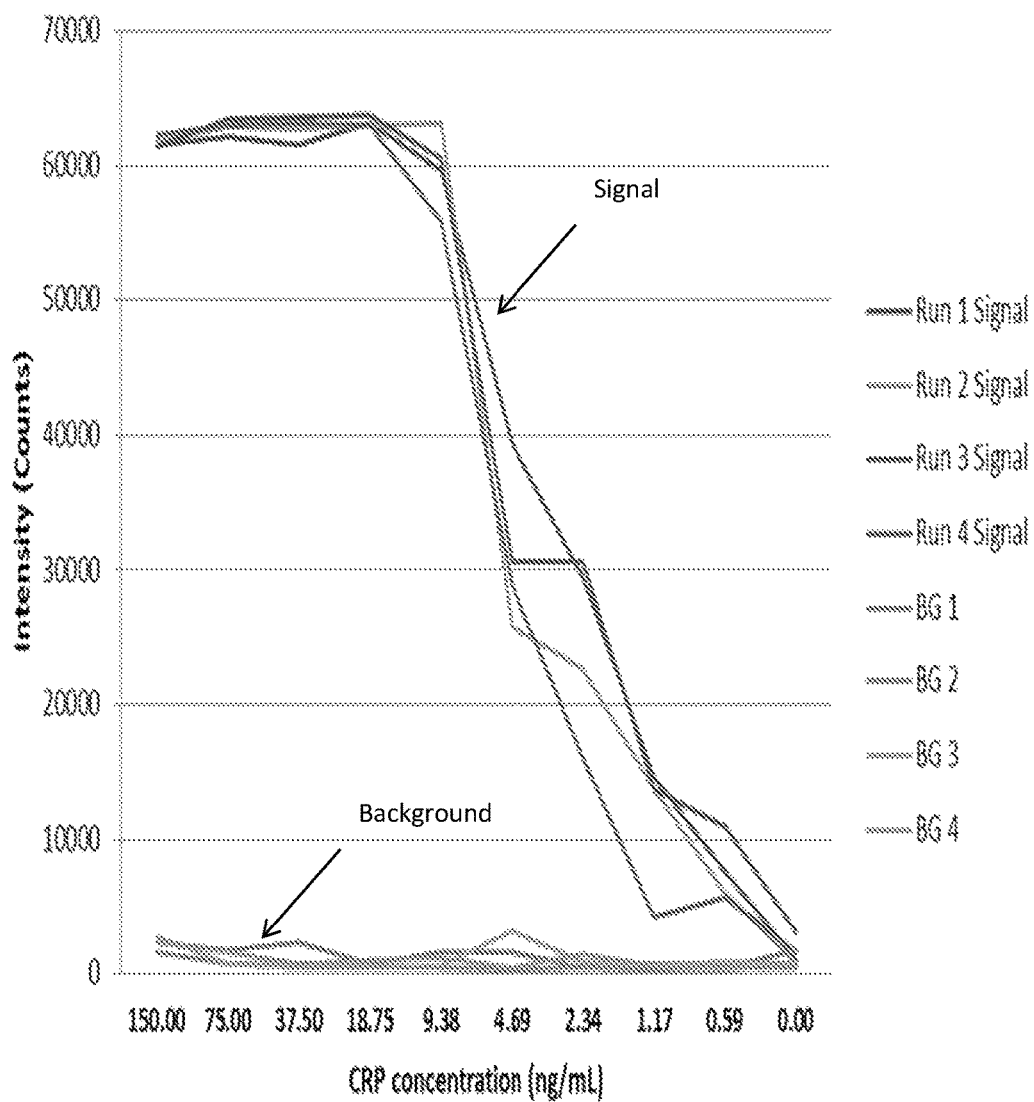
FIG. 9 provides repeat data on scans of fluorescent and background signals from a nylon thread (used in the invention) in a fluorescent microparticle labelled immunoassay when C-reactive protein was present in a titration series.

The same fluorescent CRP assay titration series was performed on a synthetic polymer thread formed from nylon-6 fibres, and it was surprisingly discovered that the LOD was much lower than for nitrocellulose or cotton. A dose response curve showing these results is included in FIG. 9. From measurements of replicate nylon threads at different dilutions down to 0.05 ng/ml, a signal:background ratio of >3.0 was measured. It is therefore expected that the LOD for CRP on a nylon thread would be approximately 50 pg/ml—approximately 187× lower than for conventional nitrocellulose membranes. This surprising finding was very significant since many diagnostic assays require high diagnostic sensitivity. For example, the measurement of the cardiac Troponin I marker (to diagnose acute myocardial infarctaion) requires a sensitivity of 100 pg/ml or better, and hence it is considered that a synthetic thread (such as nylon) would allow a rapid test for this diagnostic marker to be used in the emergency room, whereas a conventional nitrocellulose membrane would not be suitable.

Although not wishing to be bound by any theory, it is believed that the high sensitivity of the nylon thread is obtained because the 300 nm europium beads were not entrapped in the interstitial voids (202) between the nylon filaments (203) as shown in FIG. 13. This leads to low background readings, which in turn yields much higher signal:background ratios than nitrocellulose membranes. This observation is verified by the fact that in the case of the sample measured at 0.1 ng/ml, the background readings away from the test line were an average of 1085 counts in the case of the nylon threads, which is approximately 10× lower than for the nitrocellulose membrane at the same CRP concentration.

Figure 14:
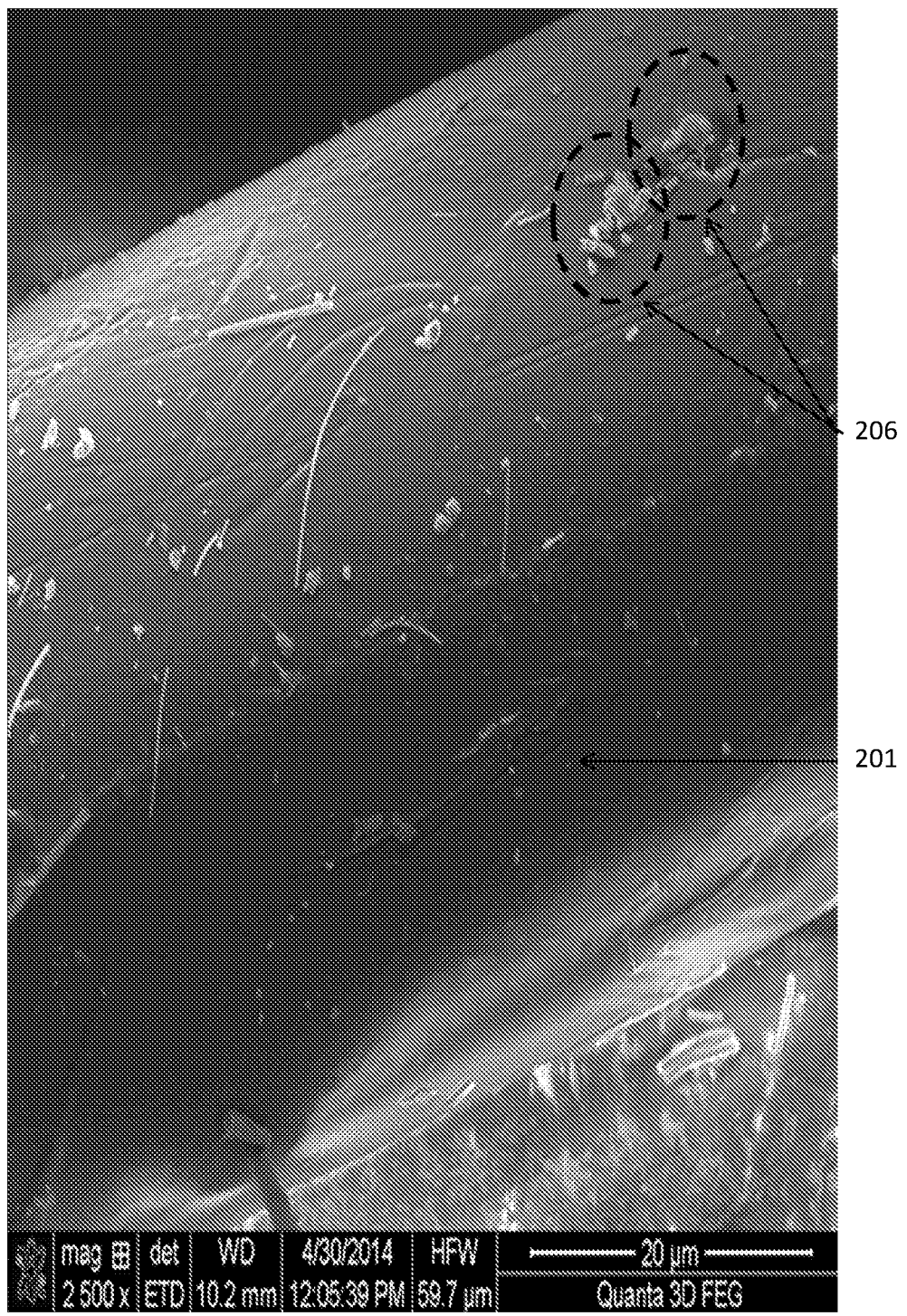
FIG. 14 is an electron microscope image at 2500× magnified image of a synthetic nylon thread at the detection zone location.

FIG. 14 shows an electron microscopy image at 2500× magnification of the detection zone location on a 40 micron diameter nylon thread with Europium microparticles bound to the thread surface in the case of a CRP assay at 12.5 ng/ml. In this image it can be seen that some of the Europium microparticles have hound to the thread surface individually (as single particles 201), however other Europium microparticles have formed larger clusters 206. Although these clusters are relatively large, they are still able to be transported by capillary wicking action through the interstitial voids 202 in the threads without becoming undesirably lodged in the thread structure at locations other than the detection or control zones.

Apart from the desirable feature of low background signals on synthetic threads, a further surprising finding in the use of synthetic threads was that the fluorescent signals at the detection and control zones were of comparable intensity to those obtained using nitrocellulose membranes. Nitrocellulose membranes are known to have a very high surface area for the capture of labelled analyte targets at the detection zone, and such high surface area is known to be a desirable feature to promote enhanced sensitivity. Threads, by contrast, are known to have a lower surface area which should, in theory, lead to considerably lower fluorescent signals from the analyte target at the test zone. However, in the case of nitrocellulose membranes, the membrane material is an opaque white colour, which means that only fluorescent microparticles near the upper surface of the membrane are able to be excited by the excitation source. However, in the case of many types of synthetic threads (including nylon threads), transparent fibres are able to be used. As shown in FIG. 13, this means that excitation light 204 is able to penetrate through several threads 203 to excite Europium microparticles in all of the interstitial voids 202. Furthermore, the fluorescent emitted light 205 from the microparticles is able to penetrate through several threads back to the detection source. In this way, the synthetic threads used in this invention allow the fluorescent signals to be read through the entire depth of the thread structure, whereas in nitrocellulose membranes this is only possible at the surface. We believe that this ability to be able to read through the depth of the threads compensates for the loss of surface area for binding available in the threads.

Consequently, it has surprisingly been found that a rapid fluorescent lateral flow immunoassay utilising a microparticle encapsulated with a fluorescent marker has significantly improved diagnostic sensitivity and repeatability when the assay is performed using a synthetic polymer thread as a porous carrier material (i.e. wicking substrate) instead of conventional nitrocellulose membranes. Immunofluorescent assays comprising synthetic polymer threads as porous carrier materials, particularly when used with fluorescently labelled microparticle, can therefore be used for rapid diagnostic assays where high sensitivity is required or where the quantification of an analyte target may also be necessary.

The invention claimed is:

1. A lateral flow immunofluorescent assay device for use in performing an immunofluorescent assay on a sample, wherein the device comprises:
   one or more synthetic polymer threads, wherein the one or more synthetic polymer threads each comprise at least:
     a sample loading zone,
     a detection zone comprising an immobilised capture reagent that has affinity for a predetermined analyte in the sample, and
     optionally an intermediate zone disposed between the sample loading zone and the detection zone;
   wherein the one or more synthetic polymer threads are capable of carrying a fluid sample by capillary action from at least the sample loading zone to the detection zone; and
   wherein the device comprises a fluorescent detection reagent comprising fluorescently labelled microparticles that are associated, linked or coordinated to an analyte binding reagent that has affinity for a predetermined analyte in the sample, wherein the fluorescent detection reagent is reversibly immobilised to the device.

2. The device of claim 1, wherein the one or more synthetic polymer threads are formed from synthetic polymers selected from the group consisting of polyamides, polyesters, polyethers, polyolefins, polycarbonates and polyurethanes.

3. The device of claim 2, wherein the one or more synthetic polymer threads are formed from nylon.

4. The device of claim 1, wherein the fluorescently labelled microparticles are fluorescently labelled polymer microparticles comprising rare earth metal complexes selected from the group consisting of europium, terbium and samarium, metal chelates thereof, and combinations thereof.

5. The device of claim 1, wherein the microparticles have an average diameter (in nm) in the range of 100 to 5000.

6. The device of claim 1, wherein the device is a multiplexed assay device for determining the presence or level of two or more predetermined analytes in the sample.

7. The device of claim 1, wherein the one or more synthetic polymer threads are each connected at the sample loading zone and form independent thread lanes.

8. The device of claim 1, wherein the sample loading zone of the thread is configured for receiving a sample premixed with fluorescent detection reagent.

9. The device of claim 1, wherein the one or more synthetic polymer threads each define an intermediate zone disposed between the sample loading zone and the detection zone, and the fluorescent detection reagent is reversibly immobilised on the intermediate zone of the device for use in labelling a predetermined analyte for detection in the detection zone.

10. The device of claim 1, wherein the fluorescent detection reagent is reversibly immobilised directly on the thread.

11. The device of claim 1, wherein the device comprises a conjugate pad in fluidic communication with the one or more synthetic threads.

12. The device of claim 11, wherein the fluorescent detection reagent is reversibly immobilised on the conjugate pad.

13. A system for performing an immunofluorescent assay on a sample comprising:
   a lateral flow immunoassay device comprising one or more synthetic polymer threads, wherein the one or more synthetic polymer threads each comprise at least:
     a sample loading zone,
     a detection zone comprising an immobilised capture reagent having affinity for a predetermined analyte in the sample, and
     optionally an intermediate zone disposed between the sample loading zone and the capture zone, wherein the one or more synthetic polymer threads are capable of carrying a fluid sample by capillary action from at least the sample loading zone to the detection zone;
   a fluorescent detection reagent for binding to a predetermined analyte in the sample to form a fluorescently labelled analyte, wherein the fluorescent detection reagent comprises fluorescently labelled microparticles associated, coordinated or linked to an analyte binding reagent that has affinity for a predetermined analyte in the sample; and
   a fluorescent excitation source and detector for use in detecting a predetermined analyte that is bound to the fluorescent detection reagent and immobilised in the detection zone of the device by the capture reagent.

14. The system of claim 13, wherein the one or more synthetic polymer threads are formed from synthetic polymers selected from the group consisting of polyamides, polyesters, polyethers, polyolefins, polycarbonates and polyurethanes.

15. The system of claim 13, wherein the one or more synthetic polymer threads are formed from nylon.

16. The system of claim 13, wherein the microparticles have an average diameter (in nm) in the range of 100 to 5000.

17. The system of claim 13, wherein the sample loading zone of the thread is for receiving a sample premixed with fluorescent detection reagent.

18. The system of claim 13, wherein the one or more synthetic polymer threads each define an intermediate zone disposed between the sample loading zone and the detection zone, and the fluorescent detection reagent is reversibly immobilised on the intermediate zone of the device for use in labelling a predetermined analyte for detection in the detection zone.

19. The system of claim 13, wherein the fluorescent detection reagent is reversibly immobilised directly on the thread.

20. The system of claim 13 for use in quantitatively measuring the concentration of the analyte in the sample.

21. A kit for performing an immunofluorescent assay on a sample comprising:

a lateral flow immunoassay device comprising one or more synthetic polymer threads, wherein the one or more synthetic polymer threads each comprise at least:
        a sample loading zone,
        a detection zone comprising an immobilised capture reagent having affinity for a predetermined analyte in the sample, and
        optionally an intermediate zone disposed between the sample loading zone and the capture zone, wherein the one or more synthetic polymer threads are capable of carrying a fluid sample by capillary action from at least the sample loading zone to the detection zone; and
    a fluorescent detection reagent for binding to a predetermined analyte in the sample to form a fluorescently labelled analyte, wherein the fluorescent detection reagent comprises fluorescently labelled microparticles associated, coordinated or linked to an analyte binding reagent that has affinity for a predetermined analyte in the sample.

\* \* \* \* \*